(12) United States Patent
Hennebelle

(10) Patent No.: US 9,671,329 B2
(45) Date of Patent: Jun. 6, 2017

(54) METHOD AND DEVICE FOR MEASURING THE COLOUR OF AN OBJECT

(71) Applicant: Franck Hennebelle, Paris (FR)

(72) Inventor: Franck Hennebelle, Paris (FR)

(73) Assignee: COLOR GRAIL RESEARCH, Paris (FR)

( * ) Notice: Subject to any disclaimer, the term of this patent is extended or adjusted under 35 U.S.C. 154(b) by 223 days.

(21) Appl. No.: 14/378,338

(22) PCT Filed: Feb. 14, 2013

(86) PCT No.: PCT/EP2013/053000
§ 371 (c)(1),
(2) Date: Aug. 13, 2014

(87) PCT Pub. No.: WO2013/120956
PCT Pub. Date: Aug. 22, 2013

(65) Prior Publication Data
US 2015/0062584 A1    Mar. 5, 2015

(30) Foreign Application Priority Data

Feb. 17, 2012 (FR) .................................. 12 51484
May 18, 2012 (FR) .................................. 12 54559
Jul. 31, 2012 (FR) .................................. 12 57403

(51) Int. Cl.
*G01J 3/46*        (2006.01)
*G01N 21/25*       (2006.01)
(Continued)

(52) U.S. Cl.
CPC .......... *G01N 21/255* (2013.01); *G01J 3/0272* (2013.01); *G01J 3/50* (2013.01);
(Continued)

(58) Field of Classification Search
CPC ........ G01J 3/02; G01J 3/10; G01J 3/50; G01J 3/501
(Continued)

(56) References Cited

U.S. PATENT DOCUMENTS 5,659,397 A * 8/1997 Miller ................ G01N 21/4738
                                              250/341.8
2010/0067004 A1 * 3/2010 Nagashima ............... G01J 3/02
                                                356/326

FOREIGN PATENT DOCUMENTS

GB      2474701      4/2011
WO      2004/079314  9/2004

OTHER PUBLICATIONS

International Search Report dated Jul. 10, 2013, corresponding to PCT/EP2013/053000.
(Continued)

*Primary Examiner* — Abdullahi Nur
(74) *Attorney, Agent, or Firm* — Young & Thompson

(57) ABSTRACT

The present invention relates to a method for measuring the uniform diffuse reflectance $R^{OBJ}(\lambda)$ at least at one point on an object (30) using a device (10) comprising a means (11) capable of emitting color illuminants expressed in the form of luminous flux and an electronic color image sensor (12). The present invention also relates to a device (10) comprising a means (11) for emitting color illuminants expressed as luminous flux of colors and an electronic color image sensor (12), for measuring the uniform diffuse reflectance $R^{OBJ}(\lambda)$ at least at one point on an object (30) placed in a zone located opposite and substantially perpendicular to the said means (11) capable of emitting colors and located in the field of vision of the said electronic color image sensor (12) and being subjected to an external illuminant expressed as a constant and unknown external environmental luminous flux (40) denoted $I^{ext}(\lambda)$.

16 Claims, 8 Drawing Sheets

(51) Int. Cl.
- *G01J 3/50* (2006.01)
- *G01J 3/02* (2006.01)
- *G01N 21/47* (2006.01)
- *H01L 27/146* (2006.01)
- *G01J 3/12* (2006.01)

(52) U.S. Cl.
CPC .......... *G01J 3/506* (2013.01); *G01N 21/4738* (2013.01); *H01L 27/14601* (2013.01); *G01J 2003/1282* (2013.01); *G01N 2201/061* (2013.01)

(58) Field of Classification Search
USPC .................................................. 356/402–425
See application file for complete search history.

(56) References Cited

OTHER PUBLICATIONS

Stephen K. Park, et al.; "Estimation of Spectral Reflectance Curves from Multispectral Image Data"; vol. 16, No. 12, Dec. 1, 1977, p. 3107.

\* cited by examiner

METHOD AND DEVICE FOR MEASURING THE COLOUR OF AN OBJECT

FIELD OF THE INVENTION

The present invention relates to the field of colour measurement.

The present invention relates more particularly to a method of spectrometry for measuring the colour of an object that makes use of an electronic device, and to the associated device.

STATE OF THE ART

A colour is a luminous flux perceived by the human eye. It involves a spectral distribution of energy $C(\lambda)$ on a band of wavelengths, in this case $\lambda$ ranging from 380 to 780 nm in the visible range (standard observer as defined by the Commission Internationale de l'Eclairage—CIE/International Commission on Illumination 1931). In the following sections, the function that describes this spectral energy distribution shall be denoted by a letter and a $\lambda$ within brackets.

On account of the additive synthesis approach, any colour may be expressed by its chromaticity coordinates in three primary colours. While there are several primary colour systems, those adopted in the following sections will be the two standardised systems which are the CIE XYZ colorimetric space (and its variant CIE Yxy with chromaticity plane at constant luminance) and the CIE L*a*b space which provides the ability to estimate a colour difference with Euclidean norm known as "deltaE", which is representative of the differences in colour perceived by the human eye. The "gamut" (limits) of these two spaces covers the entire human visible range. Reference will also be made to the trichromatic sRGB space corresponding to the reference gamut of most of the electronic equipment currently available. The gamut of sRGB does not cover the entire human visible range, especially in the blue-green spectrum.

The colour of an object results from the interactions between an incident luminous flux and the surface of the said object. Three phenomena vie with each other to give the material the appearance by which it is known: absorption, specular reflection and diffuse reflection. Specular reflection occurs on the surface of the object. There is little interaction of light with the material of the object—and in particular with its pigments. The colour of the light reflected is thus close to the light received, but the energy reflected is concentrated in a lobe centred in the theoretical direction defined by the Snell-Descartes laws. In contrast, diffuse reflection occurs at greater depth. The light emitted is tinged with the colour of the pigments and the energy reflected is independent of the direction of observation. In other words, the specular reflection is the shining component of a surface and the diffuse reflection is the matte and coloured component of a surface.

Consequently, the colour of an object thus depends on two independent factors: the illumination to which the object is subjected and the nature of the surface of the object. This latter is characterised by the "bidirectional spectral reflectance" function. It is defined as the ratio between the luminance reflected from the surface and the illumination of the latter. The value of this function depends on the wavelength $\lambda$, on the direction of the incident light and the direction of observation. The uniform diffuse reflectance of the object $R^{OBJ}(\lambda)$, corresponding to the diffuse reflection, depends only on the wavelength $\lambda$. It is this that gives the colour information in the chromatic sense, outside of the shine phenomenon.

This is why the colour of an object may be characterised 1) by the light reflected under a given illuminant (for example the CIE L*a*b chromaticity coordinates under an illuminant D50 in a dark room), or better still, 2) by its spectral reflectance $R^{OBJ}(\lambda)$. The first method requires relatively simple measuring devices (including colour charts, tri-stimulus colorimeters, among others), but with a high risk of metamerism (this method is not very accurate). Its use is generally restricted to the monitoring of deviations from a standard or benchmark colour along a manufacturing process (printing, textile, graphic arts, etc). The second method requires more sophisticated devices (including among others, diffraction spectrometer, spectrometer with dual photoreceptors in parallel); it is not affected by metamerism (this method is very accurate) and makes it possible to simulate the perception of colour under different illuminants (interior, exterior). It is designed for use by demanding professionals and in design activities.

All these devices are not compatible with mobile, hand held and unplanned use as with a mobile phone or a tablet computer that can be taken anywhere. Their use is relatively complicated, not to mention the significant additional cost that they represent.

In contrast, applications for measurement of colour currently available on mobile phones and tablets (iOS, Android, etc) do not require additional specialised equipment, but these applications do not provide for an accurate measurement of colours. Indeed, they rely solely on the use of the colour image sensor of the device (array of tri-stimulus photodetectors, Bayer red-green-blue matrix) with a programme for the computing of white balance. Their perception of the colours of objects is thus distorted by the unknown variability of ambient light.

Known techniques from the prior art include the emissive diffraction spectrometer and a method for determination of the function of spectral reflectance of the object: the device produces a standardised white illuminant $S(\lambda)$ in the direction of the target, the illuminant is reflected on the object, then passes through a prism to be diffracted towards several dozens of photodetectors (one for each sub-spectrum) which provides the ability to interpolate $E(\lambda)$, where $R^{OBJ}(\lambda)=E(\lambda)/S(\lambda)$. The operation of measuring the colour of an object with this method of the prior art is carried out with a specially developed boxed unit and with a process requiring a cover for masking any unknown external illuminant. In addition, this type of spectrometer cannot be used to perform spectrometric photography.

The prior art also provides knowledge from the U.S. Pat. No. 5,963,333, of a spectrometer with LED and two photoreceptors arranged in parallel, a spectrometer detection unit and a method for determining the function of spectral reflectance of the object. The measurement of colour of an object with this method of the prior art is carried out by means of a specially developed boxed unit and with a process requiring a cover for masking any unknown external illuminant. In addition, this type of spectrometer cannot be used to perform spectrometric photography.

The prior art also provides knowledge through the patent application PCT No WO 2004/079314, of a colorimeter, a colorimeter detection unit and a method for determining the colour of an object by calculating a deviation from a standard colour. The operation of measuring the colour of an object with this method of the prior art is carried out with a specially developed boxed unit, a process requiring a cover for masking any unknown external illuminant, and a method that is incapable of measuring a spectral reflectance function in the strictest sense.

The prior art also provides knowledge through the UK patent application No GB2474701A, of a colorimeter, a colorimeter detection unit and a method for determining the colour of an object by calculating a deviation from a standard colour. The operation of measuring the colour of an object with this method of the prior art is carried outby means of a telephone equipped with a screen for emitting flashes of colour and a camera unit on the opposite face. The measurement of colour with this method of the prior art is performed with specially developed waveguides (sets of mirrors, optical fibres, etc), a process requiring a cover or waveguides for masking any unknown external illuminant, and a method that is incapable of measuring a spectral reflectance function in the strictest sense.

OVERVIEW OF THE INVENTION

The present invention seeks to overcome the drawbacks of the prior art by providing a method for measuring the colour of an object through spectrometry by using as a transmitter a means capable of emitting colour illuminants, and as a receiver, an electronic colour image sensor, the two situated side by side, with or without the presence of an unknown external illuminant (but constant for all the flashes).

In principle, the present invention operates contrary to a diffraction emission spectrometer: instead of generating a single standardised illuminant and analysing it with several dozens of photodetectors, the present invention generates several dozens of standardised illuminants and analyses them with only three photodetectors.

To this end, the present invention relates, in its most general sense, to a method for measuring the uniform diffuse reflectance $R^{OBJ}(\lambda)$ at least at one point of an object by using a device comprising a means capable of emitting coloured illuminants expressed in the form of luminous flux and an electronic colour image sensor, characterised in that it comprises the following steps:

placing of the said object in a zone located opposite and substantially perpendicular to the said means capable of emitting coloured illuminants in the form of luminous fluxes of colours and located in the field of vision of the said electronic colour image sensor, the said object also being subjected to an external illuminant in the form of a constant and unknown external environmental luminous flux $I^{ext}(\lambda)$, where $\lambda$ denotes the wavelength; emission by the said means of a series of N illuminants $S^{source}(\lambda)_i$ (with N being a natural number greater than one, i varying from 1 to N and $\lambda$ being the wavelength), $S^{source}(\lambda)_i$ being known as a function of the input parameters of the said means capable of emitting luminous fluxes of colours, capture by the said electronic colour image sensor of the luminous flux reflected at least at one point of the said object and entering in the sensor, the said luminous flux being denoted as $E^{capteur}(\lambda)_i$, with N being a natural number strictly greater than two, i varying from 1 to N and $\lambda$ being the wavelength; and obtaining of N equations "$E_i$": $E^{capteur}(\lambda)_i = R^{OBJ}(\lambda)*(I^{ext}(\lambda)+S^{source}(\lambda)_i)$ due to the additive nature of the light wave and by definition of the uniform diffuse reflectance $R^{OBJ}(\lambda)$ at least at one point of the object; and determination by the said device of the two unknown continuous functions $R^{OBJ}(\lambda)$ and $I^{ext}(\lambda)$ by solving the system of N equations $E_i$:

by integrating each equation $E_i$ on the intersection of the source and sensor spectra, by denoting x, y and z the sensitivities in the colorimetric base selected, each equation $E_i$ then generating three "$E_i$ integrated" equations:

$$\int E^{capteur}(\lambda)_i * x(\lambda) * d\lambda = \int R^{OBJ}(\lambda)*(I^{ext}(\lambda)+S^{SOURCE}(\lambda)_i) * x(\lambda) * d\lambda$$

$$\int E^{capteur}(\lambda)_i * y(\lambda) * d\lambda = \int R^{OBJ}(\lambda)*(I^{ext}(\lambda)+S^{SOURCE}(\lambda)_i) * x(\lambda) * d\lambda$$

$$\int E^{capteur}(\lambda)_i * z(\lambda) * d\lambda = \int R^{OBJ}(\lambda)*(I^{ext}(\lambda)+S^{SOURCE}(\lambda)_i) * x(\lambda) * d\lambda$$

by calculating the numerical value corresponding to the left-hand side of the Ei integrated equations with the use of the output parameters of the digital image sensor; and by expressing the two unknown continuous functions $R^{OBJ}(\lambda)$ and $I^{ext}(\lambda)$ with the use of a finite number of interpolation points $(\lambda_j, y_j)$ connected by at least one interpolation function $s(\lambda)$ for maintaining the continuous nature of the said unknown continuous functions $R^{OBJ}(\lambda)$ and $I^{ext}(\lambda)$, the $\lambda_j$ being selected wavelengths in the intersection of the source and sensor spectra and being input parameters of the method, chosen to minimize the number of interpolation points for a given precision; and by finding the parameters $y_j$ of the functions $R^{OBJ}(\lambda)$ and $I^{ext}(\lambda)$ that minimize the least squares system $\|A-*-X-B\|_2$ resulting from the $E_i$ integrated equations.

Thus, the method according to the present invention provides the ability to precisely measure the uniform diffuse reflectance of an object at least at one point, and this in an optimised manner compared to the solutions described in the prior art. In addition, the present invention works very well with daily use mobile or handheld devices.

Advantageously, the said method further includes a step of determining the value of the external illuminant $I^{ext}(\lambda)$.

Preferably, the said method includes in addition, a step of transcription of the function $R^{OBJ}(\lambda)$ of uniform diffuse reflectance at least at one point of the object into the CIE XYZ coordinates for a given illuminant.

According to one embodiment, the number of flashes is of the same order of magnitude as the number of interpolation points for determining the values of the uniform diffuse reflectance $R^{OBJ}(\lambda)$ at least at at one point of the object and of the external illuminant $I^{ext}(\lambda)$.

According to one variant, the said method includes a step of determining the values of the uniform diffuse reflectance $R^{OBJ}(\lambda)$ at least at one point of the object and the external illuminant $I^{ext}(\lambda)$ in several spectral bands.

According to one embodiment, the said device makes use of a screen for emitting flashes of colour and an electronic image sensor for sensing and capturing the light reflected by the target object.

According to a particular mode of implementation, the said device is a camera unit or a camera with in built or removable flash.

Advantageously, the said device implements waveguides for ensuring effective transiting of the emission and reception of flashes of colours.

According to one variant, the said method is implemented in order to take spectrometric photographs of objects and to make chromatic adjustments (balancing of whites) at will.

According to another variant, the said method according to one of the preceding claims, characterised in that it is implemented in order to measure the colour of an element included in the following group: materials, solids, liquids, gases, paintings, tapestries, graphics, textiles, plastics, woods, metals, soils, minerals, plants and foods.

According to one embodiment, the method is implemented for the measurement of colours, for medical or cosmetic purposes with respect to humans and living beings/organisms, of at least one element included in the following group: skin, pimples, moles, hair, fur/hair coat, makeup, and teeth.

According to a variant, the said method is implemented for the use of colour barcodes, of one or more dimensions.

According to a particular mode of implementation, the method is implemented with a view to assisting people having colour blindness and/or who are blind.

The present invention also relates to a device comprising the means capable of emitting colour illuminants in the form of luminous flux of colours and an electronic colour image sensor, for measuring the uniform diffuse reflectance $R^{OBJ}(\lambda)$ at least at one point of an object placed in a zone located opposite and substantially perpendicular to the said means capable of emitting colours and located in the field of vision of the said electronic colour image sensor, and also being subjected to an external illuminant in the form of a constant and unknown external environmental luminous flux denoted as $I^{ext}(\lambda)$, characterised in that it comprises the means for:

emitting a series of N illuminants $S^{source}(\lambda)_i$ (with N being a natural number greater than two, i varying from 1 to N and $\lambda$ being the wavelength), $S^{source}(\lambda)_i$ being known as a function of the input parameters of the said means capable of emitting luminous fluxes of colours, capture by the said electronic colour image sensor (12) of the luminous flux reflected at least at one point of the said object and entering in the sensor, the said luminous flux being denoted as $E^{capteur}(\lambda)_i$, with N being a natural number greater than one, i varying from 1 to N and $\lambda$ being the wavelength; and obtaining of N equations $(E_i): E^{capteur}(\lambda)_i = R^{OBJ}(\lambda) * (I^{ext}(\lambda) + S^{source}(\lambda)_i)$ due to the additive nature of the light wave and by definition of the uniform diffuse reflectance $R^{OBJ}(\lambda)$ at least at one point of the object; and determining the two unknown continuous functions $R^{OBJ}(\lambda)$ and $I^{ext}(\lambda)$ by solving the system of N equations $E_i$:
    by integrating each equation $E_i$ on the intersection of the source and sensor spectra, by denoting x, y and z the sensitivities in the colorimetric base selected, each equation $E_i$ then generating three "$E_i$ integrated" equations:

$$\int E^{capteur}(\lambda)_i * x(\lambda) * d\lambda = \int R^{OBJ}(\lambda) * (I^{ext}(\lambda) + S^{SOURCE}(\lambda)_i) * x(\lambda) * d\lambda$$

$$\int E^{capteur}(\lambda)_i * x(\lambda) * d\lambda = \int R^{OBJ}(\lambda) * (I^{ext}(\lambda) + S^{SOURCE}(\lambda)_i) * y(\lambda) * d\lambda$$

$$\int E^{capteur}(\lambda)_i * x(\lambda) * d\lambda = \int R^{OBJ}(\lambda) * (I^{ext}(\lambda) + S^{SOURCE}(\lambda)_i) * z(\lambda) * d\lambda$$

by calculating the numerical value corresponding to the left-hand side of the Ei integrated equations with the use of the output parameters of the digital image sensor; and
    by expressing the two unknown continuous functions $R^{OBJ}(\lambda)$ and $I^{ext}(\lambda)$ with the use of a finite number of interpolation points $(\lambda_j, y_j)$ connected by at least one interpolation function $s(\lambda)$ for maintaining the continuous nature of the said unknown continuous functions $R^{OBJ}(\lambda)$ and $I^{ext}(\lambda)$, the $\lambda_j$ being selected wavelengths in the intersection of the source and sensor spectra and being input parameters of the method, chosen for minimizing the number of interpolation points for a given precision; and
    by finding the parameters $y_j$ of the curves $R^{OBJ}(\lambda)$ and $I^{ext}(\lambda)$ that minimize the least squares system $\|A*X-B\|_2$ resulting from the $E_i$ integrated equations.

BRIEF DESCRIPTION OF THE DRAWINGS

The invention will be better understood with the aid of the description, provided here below for purely explanatory purposes, of an embodiment of the invention, with reference to the Figures in which.

DETAILED DESCRIPTION OF EMBODIMENTS OF THE INVENTION

By way of a preliminary remark, it should be noted that the notations in this section are as follows: sensor=electronic colour image sensor (the video function is not used in the context of calibration and benchmarking, only the taking of static images is used), source=source of illuminants/flashes of colours (screen, diode(s), laser(s), etc). (R, G, B)$^{source}$i=non-linear input chrominance parameters of the source of colour illuminants (RGBW$^{source}$ i or RGBY$^{source}$ i for the devices with 4 and more primaries), BL$^{source}$ i=non-linear input luminance parameter of the source of colour illuminants (for example the back lighting of a LCD screen); (R, G, B)$^{capteur}$ i=non linear output chrominance parameters of the luminous flux captured by the colour image sensor, BV$^{capteur}$ i=non linear output luminance parameter of the luminous flux captured by the colour image sensor (for example Brightness Value of Japanese standardEXIF—Exchangeable Image File Format); OBJ=colour object to be measured; EXT=external environmental illuminant; R/G/B=equation valid for each primaryred (red) or green (green) or blue (blue); OBJ/EXT=equation valid for the coloured objector foroutside external illuminant; x/y/z $(\lambda)$=equation valid for each spectralsensitivity $X(\lambda)$, $y(\lambda)$ and $z(\lambda)$; spectralsensitivities of the CIE 1931 standard observer=$x^{EC\_CIE\_1931}(\lambda)$, $y^{EC\_CIE\_1931}(\lambda)$, $z^{EC\_CIE\_1931}(\lambda)$ for $\lambda \in$ [380 nm; 780 nm]; spectral sensitivities of the electronic colour image sensor: $x^{EC\_capteur}(\lambda)$ $y^{EC\_capteur}(\lambda)$, $z^{EC\_capteur}(\lambda)$, The superscript notations EC_XXX signify that it is situated in the XXX colorimetric space.

In the figures and the exemplary embodiment described here below, the means 11 capable of emitting colours is an emissive display screen. It is understood that this means 11 capable of emitting colours may also be one or more multicolour diode(s), one or more multicolour laser(s), one or more coloured flash(es) or any other means capable of emitting "colours" (a "colour"=a spectral energy function in the range of wavelength considered). Moreover, in the figures and the exemplary embodiment described here below, the colour of the object is reduced to the uniform diffuse reflectance. It is understood that the said method is capable of capturing the other components of reflectance, in particular specular reflectance for objects with high shine and satin like shine via the display on the screen of a white figure on a black background and the detection of the resultant specular reflection lobe by a gradient analysis in the image focal plane of the colour image sensor.

Figure 1:
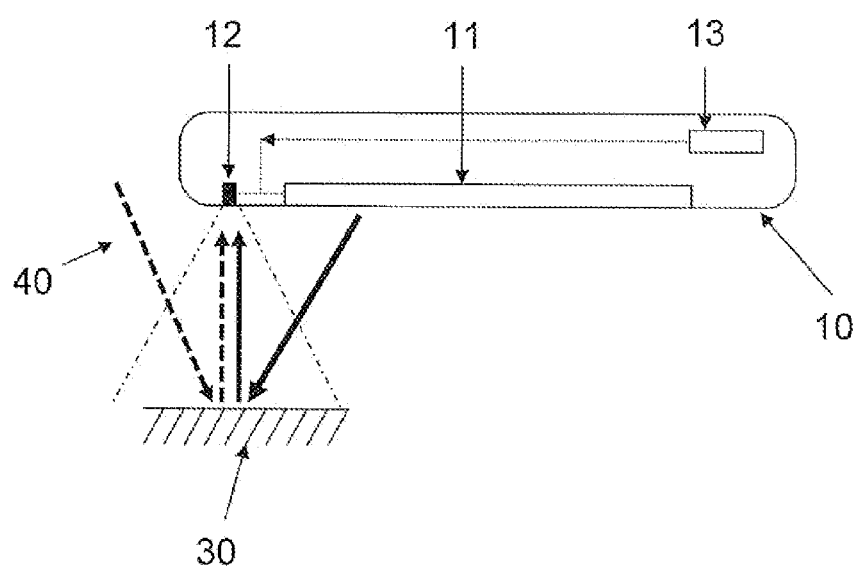
FIG. 1 schematically illustrates the device according to the present invention.

FIG. 1 represents on a schematic cross section the device 10 according to the invention for measuring the colours of an object and the external surrounding light: the object 30 to be measured of colour $R^{OBJ}(\lambda)$; the means capable of emitting colours 11 capable of emitting N known illuminants $S^{source}(\lambda)_i$; the external surrounding light 40 $I^{ext}(\lambda)$; the electronic colour image sensor 12 characterising in chrominance and luminance the luminous flux reflected $E^{capteur}(\lambda)_i$; the computer application 13 "colorimetrically pre-standardised" which controls the assembly and interacts with the operator.

In one embodiment, the computer application 13 is partially or totally distributed in the network or "cloud" ("cloud" in Anglo-Saxon terminology).

Figure 2:
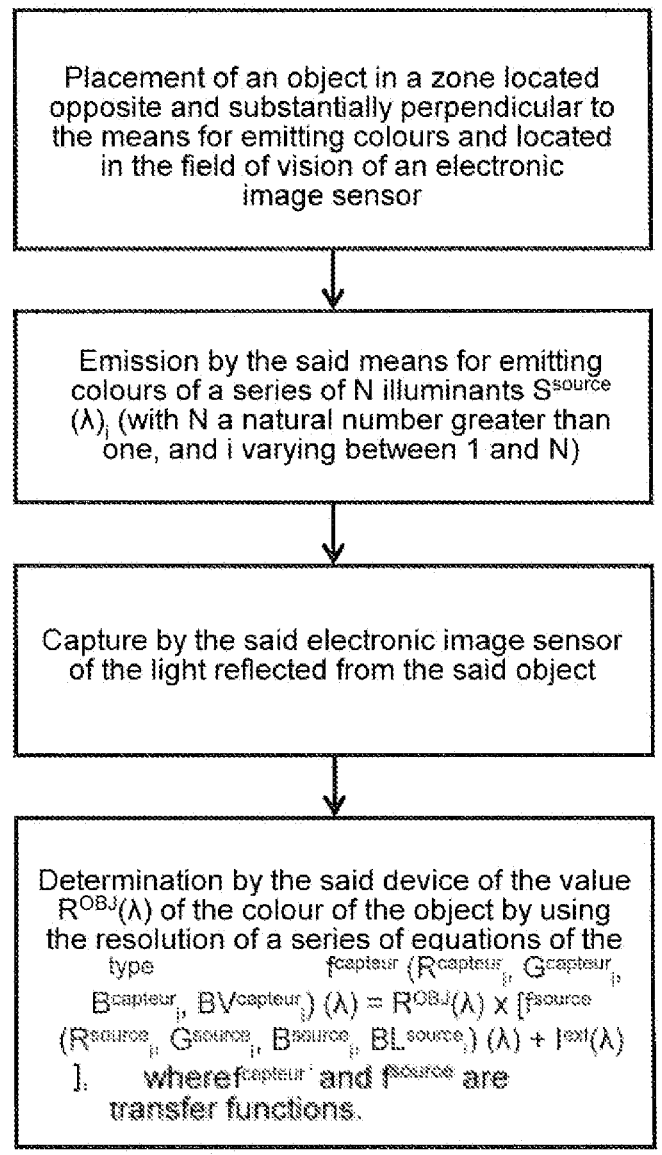
FIG. 2 represents the different steps of the method according to the present invention.

FIG. 2 represents the various different steps of the method according to the present invention:
  placing of the said object in a zone 30 located opposite and substantially perpendicular to the said means 11 capable of emitting coloured illuminants in the form of luminous fluxes of colours and located in the field of vision of the said electronic colour image sensor 12 the said object 30 being subjected to an external illuminant in the form of a constant and unknown external environmental luminous flux 40 $I^{ext}(\lambda)$, where $\lambda$ denotes the wavelength; emission by the said means 11 of a series of N illuminants $S^{source}(\lambda)_i$ (with N being a natural number greater than one, i varying from 1 to N and $\lambda$ being the wavelength). $S^{source}(\lambda)_i$ being known as a function of the input parameters of the said means 11 capable of emitting luminous fluxes of colours, capture by the said electronic colour image sensor 12 of the luminous flux reflected at least at one point of the said object 30 and entering in the sensor, the said luminous flux being denoted as $E^{capteur}(\lambda)_i$, with N being a natural number greater than one, i varying from 1 to N and $\lambda$ being the wavelength; and obtaining of N equations "$E_i$":$E^{capteur}(\lambda)_i = R^{OBJ}(\lambda)*(I^{ext}(\lambda)+S^{source}(\lambda)_i)$ due to the additive nature of the light wave and by definition of the uniform diffuse reflectance $R^{OBJ}(\lambda)$ at least at one point of the object 30; and
  determination by the said device 10 of the two unknown continuous functions $R^{OBJ}(\lambda)$ and $I^{ext}(\lambda)$ by solving the system of N equations $E_i$:
    by integrating each equation $E_i$ on the domain of the visible range of the sensor, by denoting x, y and z the sensitivities in the colorimetric base selected, each equation $E_i$ then generating three "$E_i$ integrated" equations:

$$\int E^{capteur}(\lambda)_i * x(\lambda) * d\lambda = \int R^{OBJ}(\lambda)*(I^{ext}(\lambda)+S^{source}(\lambda)_i)*x(\lambda)*d\lambda$$

$$\int E^{capteur}(\lambda)_i * x(\lambda) * d\lambda = \int R^{OBJ}(\lambda)*(I^{ext}(\lambda)+S^{source}(\lambda)_i)*y(\lambda)*d\lambda$$

$$\int E^{capteur}(\lambda)_i * x(\lambda) * d\lambda = \int R^{OBJ}(\lambda)*(I^{ext}(\lambda)+S^{source}(\lambda)_i)*z(\lambda)*d\lambda,$$

by calculating the numerical value corresponding to the left-hand side of the Ei integrated equations with the use of the output parameters of the digital image sensor; and
    by expressing the two unknown continuous functions $R^{OBJ}(\lambda)$ and $I^{ext}(\lambda)$ with the use of a finite number of interpolation points $(\lambda_j, y_j)$ connected by at least one interpolation function $s(\lambda)$ for maintaining the continuous nature of the said unknown continuous functions $R^{OBJ}(\lambda)$ and $I^{ext}(\lambda)$, the $\lambda_j$ being selected wavelengths in the intersection of the source and sensor spectra and being input parameters of the method, chosen to minimize the number of interpolation points for a given precision; and
    by finding the parameters $y_j$ of the functions $R^{OBJ}(\lambda)$ and $I^{ext}(\lambda)$ that minimize the least squares system $\|A*X-B\|_2$ resulting from the $E_i$ integrated equations.

Figure 3:
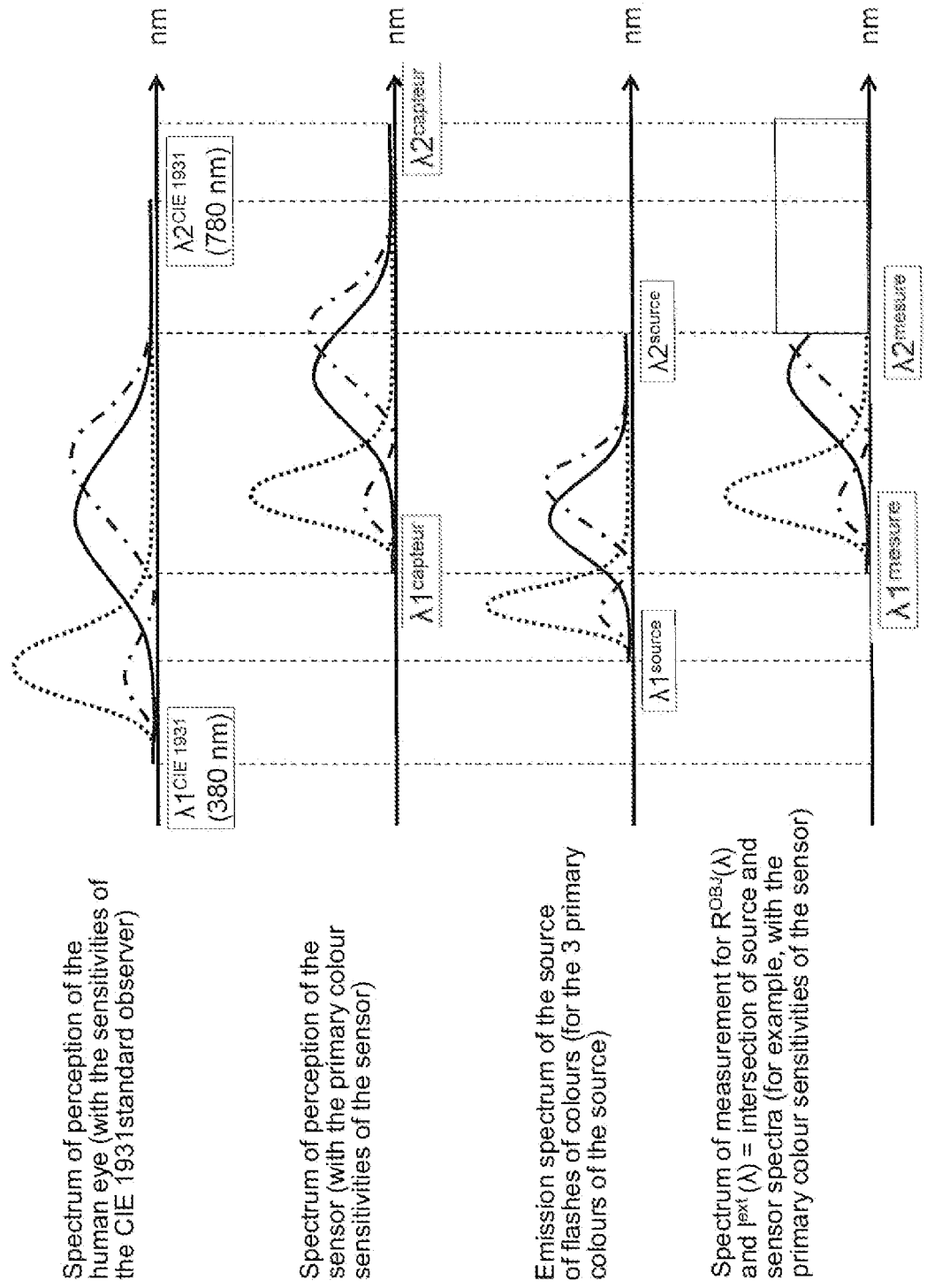
FIG. 3 describes the systematic non-overlapping of the bands of wavelengths involved in the process that is part of the method according to the present invention: human eye, sensor, source, measurement; and the FIGS. 4, 5, 6, 7 and 8 illustrate the flashing algorithm, in this case the generation of successive grids in order to distribute in as homogenous a manner as possible N flashes within the flashing triangle.

FIG. 3 describes the systematic non-overlapping of the bands of wavelengths involved in the method according to the present invention:
  Human Eye: according to the CIE 1931 standard, it perceives luminous fluxes between $\lambda 1^{CIE\ 1931}=380$ nm and $\lambda 2^{CIE\ 1931}=780$ nm with sensitivities denoted as $x/y/z^{EC\_CIE\_1931}(\lambda)$ hence the $x/y/z^{EC\_CIE\_1931}(\lambda)$ colorimetric space by integration on $[\lambda 1^{CIE\ 1931}; \lambda 2^{CIE\ 1931}]$ well known to the person skilled in the art;
  Sensor: it perceives the luminous fluxes between $\lambda 1^{capteur}$ and $\lambda 2^{capteur}$, with sensitivities denoted as $x/y/z^{EC\_capteur}(\lambda)$ hence the $x/y/z^{EC\_capteur}(\lambda)$ colorimetric space by integration on $[\lambda 1^{capteur}; \lambda 2^{capteur}]$, similar to the CIE 1931 colorimetric space. It is important to note that the spectral band of the conventional electronic image sensors (charge coupled devices—CCD, complementary metal oxide semiconductor—CMOS) covers a portion of infra-red, in addition to the human visible range (except for the presence of an infra red filter);
  Source: the source emits flashes of colours comprised in the range $[\lambda 1^{source}; \lambda 2^{source}]$, such that $\lambda 1^{source}=\min(\Sigma_{i=1}^{N}S^{source}(\lambda)_{i>0})$ and $\lambda 2^{source}=\max(\Sigma_{i=1}^{N}=S^{source}(\lambda)_{i>0})$.
    If the source is an LCD screen of a mobile phone, it is customary for the spectral range covered to be limited to [300 nm; 700 nm], that is to say significantly less wide than that of the human eye [380 nm; 780 nm];
  Measurement: The measurement of the functions $R^{OBJ}(\lambda)$ and $I^{ext}(\lambda)$ can be performed only in the intersection of the spectra of the source and the sensor that are denoted as $[\lambda 1^{mesure}; \lambda 2^{mesure}]$. Indeed, on the one hand, the sensor does not capture anything outside its integration spectrum. On the other hand, the matrix $A^T*A$ must be invertible which is satisfied when $\Sigma_{i=1}^{N}S^{source}(\lambda)_i>0$ (see the end of the detailed description and Annexe 2). The choice of sensitivities $x/y/z^{EC\_mesure}(\lambda)>0$ over $[\lambda 1^{mesure}; \lambda 2^{mesure}]$ and zero outside thereof makes it possible to create a $x/y/z^{EC\_mesure}$ colorimetric space, similar to the CIE 1931 colorimetric space. The use of the sensitivities of the sensor is always possible, those of the CIE 1931 standard also if the band $[\lambda 1^{mesure}; \lambda 2^{mesure}]$ is included in [380 nm; 780 nm].

A consequence of FIG. 3 and of the explanations that have just been given is that the method according to the invention is capable of determining the values of the uniform diffuse reflectance $R^{OBJ}(\lambda)$ and of the external illuminant $I^{ext}(\lambda)$ in spectral bands other than that of the human visible range, on condition that the source and the sensor be compatible with these bands and that the "light" maintain a wave form: ultraviolet, infrared, etc.

Figure 4:
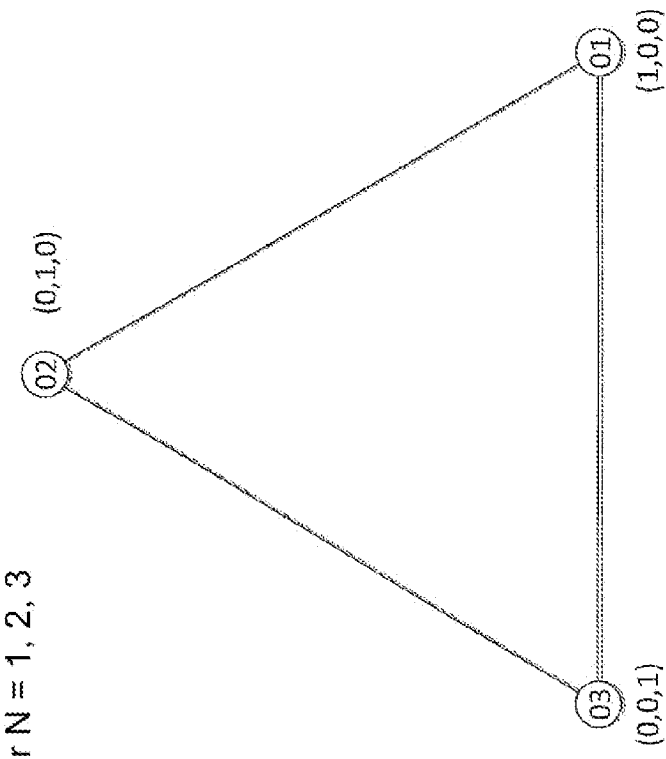
Figure 5:
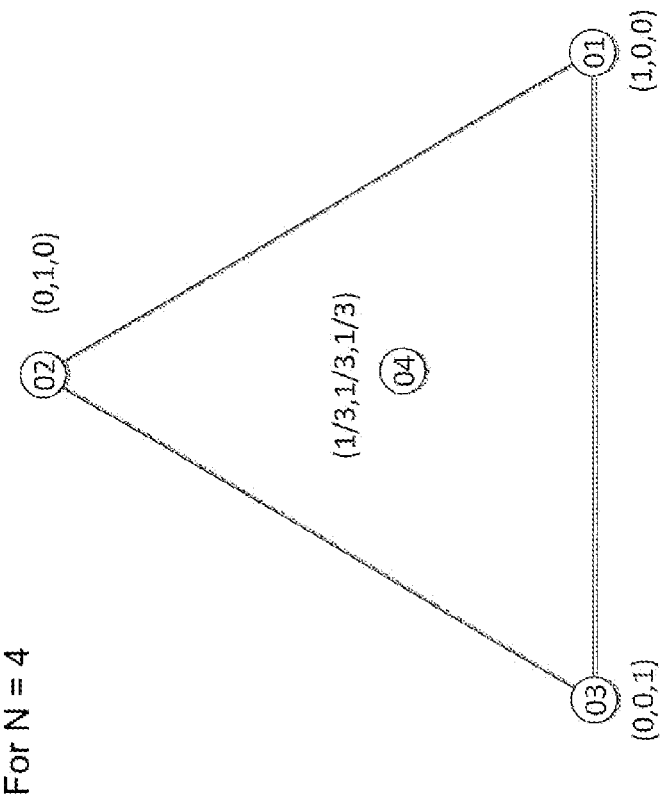
Figure 6:
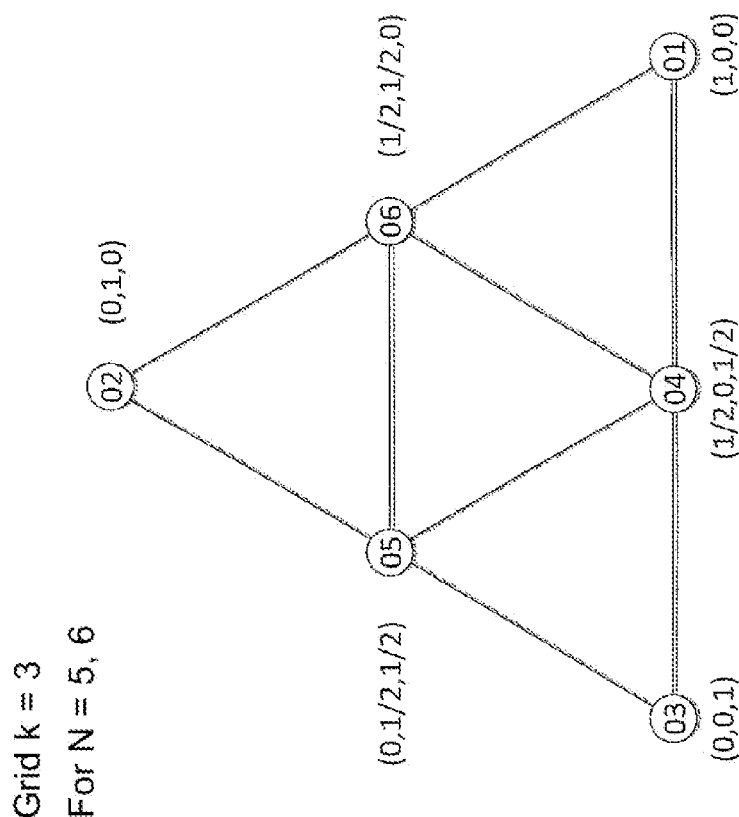
Figure 7:
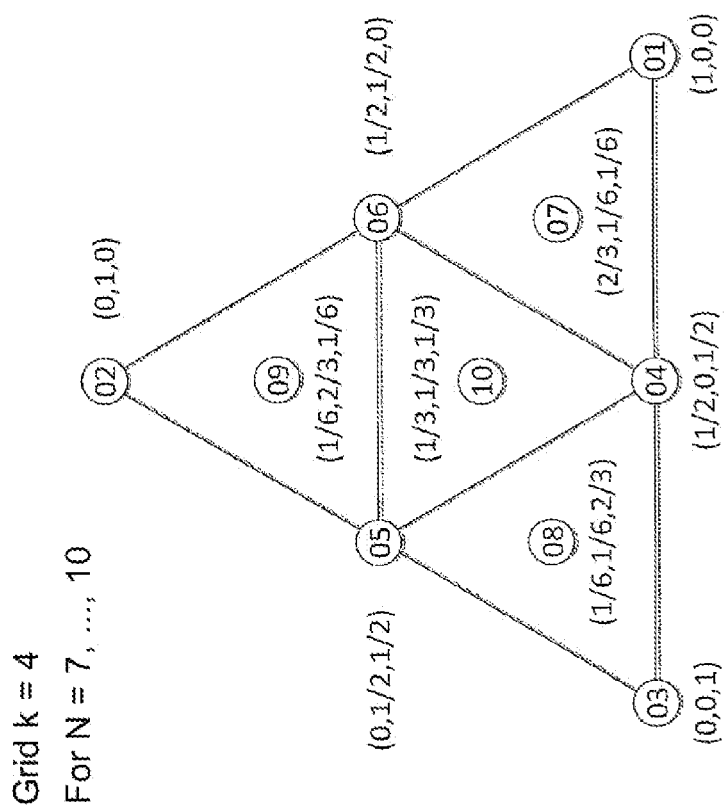
Figure 8:
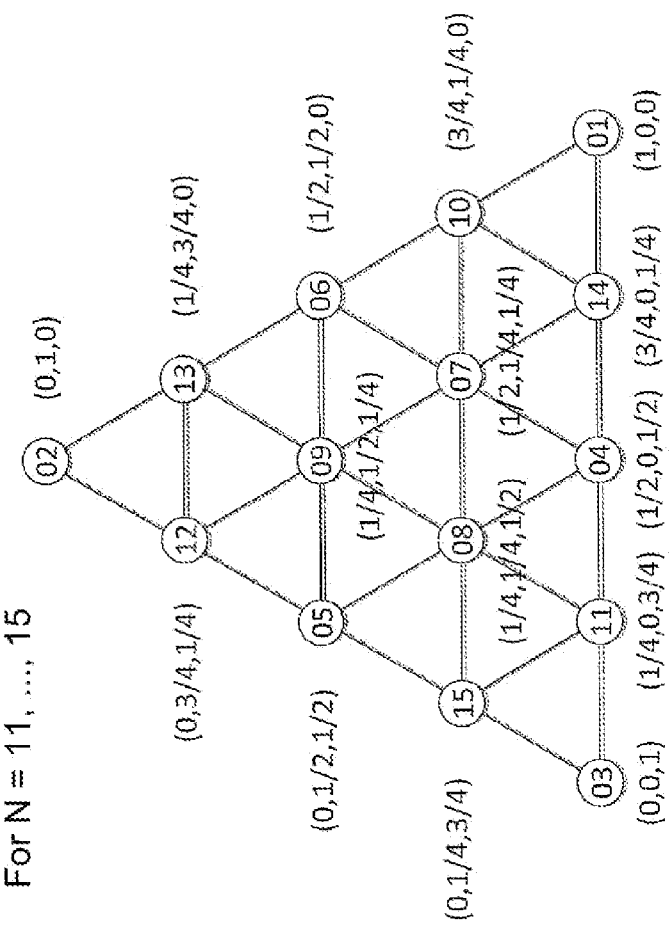

FIGS. 4, 5, 6, 7 and 8 illustrate the flashing algorithm, describing the k grids used according to a growing number of flashes N required, in order to distribute the flashes in the most homogenous manner possible in a given flashing triangle, compatible with the source and sensor gamuts. The rest of the grids k is iterative when N increases:

FIG. 4 shows the grid k=1 to be used for N comprised between 1 and 3. The position of each flash i is indicated by its number;

FIG. 5 shows the grid k=2 to be used for N=4. The position of each flash i is indicated by its number;

FIG. 6 shows the grid k=3 to be used for N comprised between 5 and 6. The position of each flash i is indicated by its number;

FIG. 7 shows the grid k=4 to be used for N comprised between 7 and 10 The position of each flash i is indicated by its number;

FIG. 8 shows the grid k=5 to be used for N comprised between 11 and 15. The position of each flash i is indicated by its number.

Now a description will be provided of the treatment process for determining the unknowns $R^{OBJ}(\lambda)$ and $I^{EXT}(\lambda)$ from the N flashes of colour.

In the embodiment shown in FIG. 1, the object to be measured 30 is placed under the source of flashes of colours 11 and in the field of vision of the electronic colour image sensor 12.

Then the source 11 successively emits a succession of flashes of colours based on the flashing algorithm described in the Annexe 1 which seeks to optimise the conditioning of the matrix A, while remaining within the screen and camera gamuts and ensuring that the external illuminant remains constant over the course of the flashes.

This algorithm takes as input a valid number of flashes N required. N depends on the number n of interpolation points required to determine the functions $R^{OBJ}(\lambda)$ and $I^{ext}(\lambda)$. At a minimum, $3*N \geq (2n+2)$ in order for the system $A*X=B$ to be property determined (see the end of the Detailed Description), thus $N \geq 2/3*(n+1)$.

The flashing algorithm returns as output a sequence of N valid flashes, with for each flash, the input parameters of the source and the output parameters of the sensor. The index of the sequence of flashes is denoted as i.

Note: If the accuracy required in order to determine the functions $R^{OBJ}(\lambda)$ and $I^{ext}(\lambda)$ is of the order of 10 nm, $N \approx n \approx 30$. Taking into account the reactivity of present day common electronic components, the entire flashing cycle takes about ten seconds at a maximum. For a non-uniform target (for example a texture), the method uses an algorithm for image stabilisation with at least one point of contrast.

Note: If the source of the flashes of colours 11 is an emissive display screen, it is capable of generating a large number of flashes of colours, typically N being able to reach $2^{24}=16.7$ million for 3×8 bit RGB systems.

For each flash i, the light emitted by the source 11 is reflected on the coloured target 30 and then it enters in the image sensor 12 which gives the equation (Ei): $E^{capteur}(\lambda)_i = R^{OBJ}(\lambda)*(S^{source}(\lambda)_i + I^{ext}(\lambda))$.

Developing the equation $(E_i)$: $E^{capteur}(\lambda)_i = R^{OBJ}(\lambda)*[S^{source}(\lambda)_i + I^{ext}(\lambda)] = R^{OBJ}(\lambda)*S^{source}(\lambda)_i + R^{OBJ}(\lambda)*I^{ext}(\lambda)$;

Let's write $I^{EXT\ REF}(\lambda) = R^{OBJ}(\lambda)*I^{ext}(\lambda)$

The equation $(E_i)$ becomes: $E^{capteur}(\lambda)_i = R^{OBJ}(\lambda)*S^{source}(\lambda)_i + I^{EXT\ REF}(\lambda)$ Firstly, the method will interpolate the functions $R^{OBJ}(\lambda)$ and $I^{EXT\ REF}(\lambda)$ with the use of a sealed cubic spline function and ($n^{OBJ/EXT\ REF}+1$) interpolation points of coordinates $[x_k = \lambda_k^{OBJ/EXT\ REF}; y_k = y_k^{OBJ/EXT\ REF}]$ for $k=0$ to $n^{OBJ/EXT\ REF}$ such that:

all the $\lambda_k^{OBJ/EXT\ REF}$ are included in the intersection of the spectra of the sensor and the source $[\lambda 1^{mesure}; \lambda 2^{mesure}]$ (see FIG. 3) with $\lambda_0^{OBJ/EXTREF} = \lambda 1^{mesure}$ and $\lambda_{n^{OBJ/EXT\ REF}}^{OBJ/EXT\ REF} = \lambda 2^{mesure}$;

the zero slope of the splines is zero at the ends: $p0=p_{n^{OBJ/EXT\ REF}}=0$

The $y_k^{OBJ/EXT\ REF}$ are the unknowns that the method will determine.

As the functions $R^{OBJ}(\lambda)$ and $I^{EXT\ REF}(\lambda)$ are sealed spline functions with zero slope at the ends, $R^{OBJ}(\lambda)$ and $I^{EXT\ REF}(\lambda)$ can be written in a linear form:

$$R^{OBJ}(\lambda) = \sum_{k=0}^{n^{OBJ}} y_k^{OBJ} * \Phi^{OBJ}(l, k, \lambda) \quad (1)$$

$$I^{EXTREF}(\lambda) = \sum_{k=0}^{n^{EXTREF}} y_k^{EXTREF} * \Phi^{EXTREF}(l, k, \lambda) \quad (2)$$

with:

l between 1 and $n^{OBJ/EXT\ REF}$ such that: $\lambda_{l-1} < \lambda \leq \lambda_l$ and $l=0$ if $\lambda = \lambda 1^{mesure}$;

$\Phi^{EXT\ REF}(l, k, \lambda) = a_k^{OBJ/EXT\ REF} + b_k^{OBJ/EXT\ REF}*(\lambda - \lambda_{l-1}) + c_k^{OBJ/EXT\ REF}*(\lambda - \lambda_{l-1})^2*(\lambda - \lambda_l) + d_k^{OBJ/EXT\ REF}*(\lambda - \lambda_{l-1})*(\lambda - \lambda_l)^2$, for $k=0$ to $n^{OBJ/EXT\ REF}$;

$a_k^{OBJ/EXT\ REF} = 0$ for $k=0$ to $l-1$;

$a_{l-1}^{OBJ/EXT\ REF} = 1$;

$a_l^{OBJ/EXT\ REF} = 0$;

$a_k^{OBJ/EXT\ REF} = 0$ for $k=l+1$ to $n^{OBJ/EXT\ REF}$;

$b_k^{OBJ/EXT\ REF} = 0$ for $k=0$ to $l-1$;

$$b_{l-1}^{OBJ/EXTREF} = \frac{1}{\lambda_{l-1} - \lambda_l};$$

$$b_l^{OBJ/EXTREF} = \frac{-1}{\lambda_{l-1} - \lambda_l};$$

$b_k^{OBJ/EXT\ REF} = 0$ for $k=l+1$ to $n^{OBJ/EXT\ REF}$;

$$c_k^{OBJ/EXTREF} = \frac{\alpha_{l,k}^{OBJ/EXTREF}}{h_{l-1}^{OBJ/EXTREF2}} \text{ for } k = 0 \text{ to } l-1;$$

$$c_{l-1}^{OBJ/EXTREF} = \frac{\alpha_{l,l-1}^{OBJ/EXTREF} - \frac{1}{\lambda_{l-1} - \lambda_l}}{h_{l-1}^{OBJ/EXTREF2}};$$

$$c_l^{OBJ/EXTREF} = \frac{\alpha_{l,l}^{OBJ/EXTREF} + \frac{1}{\lambda_{l-1} - \lambda_l}}{h_{l-1}^{OBJ/EXTREF2}};$$

$$c_k^{OBJ/EXTREF} = \frac{\alpha_{l,k}^{OBJ/EXTREF}}{h_{l-1}^{OBJ/EXTREF2}} \text{ for } k = l+1 \text{ to } n^{OBJ/EXTREF};$$

-continued $$d_k^{OBJ/EXTREF} = \frac{\alpha_{l-1,k}^{OBJ/EXTREF}}{h_{l-1}^{OBJ/EXTREF2}} \text{ for } k = 0 \text{ to } l-1;$$

$$d_{l-1}^{OBJ/EXTREF} = \frac{\alpha_{l-1,l-1}^{OBJ/EXTREF} - \frac{1}{\lambda_{l-1} - \lambda_l}}{h_{l-1}^{OBJ/EXTREF2}};$$

$$d_l^{OBJ/EXTREF} = \frac{\alpha_{l-1,l}^{OBJ/EXTREF} + \frac{1}{\lambda_{l-1} - \lambda_l}}{h_{l-1}^{OBJ/EXTREF2}};$$

$$d_k^{OBJ/EXTREF} = \frac{\alpha_{l-1,k}^{OBJ/EXTREF}}{h_{l-1}^{OBJ/EXTREF2}} \text{ for } k = l+1 \text{ to } n^{OBJ/EXTREF};$$

$h_{l-1}^{OBJ/EXT\ REF} = \lambda_{l-1} - \lambda_l$ for $l=1$ to $n^{OBJ/EXT\ REF}$;

These $\alpha_{l,k}^{OBJ/EXT\ REF}$ express the slope of the spline at the point I as a function of the $y^{OBJ/EXT\ REF} \cdot p_l^{OBJ/EXT\ REF} = \Sigma_{k=0}^{n^{OBJ/EXT\ REF}} \alpha_{l,k}^{OBJ/EXT\ REF} \cdot y_k^{OBJ/EXT\ REF}$.

These $\alpha_{(l,k)}^{OBJ/EXT\ REF}$ express the slope of the spline at the point I as a function of the $y_k^{OBJ/EXT\ REF,REF} \cdot y_k^{OBJ/EXTREF}$;

These $\alpha \alpha_{l,k}^{OBJ/EXT\ REF}$ are calculated by the inversion (by pivot) of the following linear system, characteristic of sealed cubic spline functions; they are only a function of $\lambda_l$ ($l=0$ to $n^{OBJEXT\ REF}$):

$$\frac{p_{l-1}^{OBJ/EXTREF}}{h_{l-1}^{OBJ/EXTREF}} + 2*p_l^{OBJ/EXTREF} * \left(\frac{1}{h_{l-1}^{OBJ/EXTREF}} + \frac{1}{h_l^{OBJ/EXTREF}}\right) + \frac{p_{l+1}^{OBJ/EXTREF}}{h_l^{OBJ/EXTREF}} =$$

$$3 * \left(\frac{y_{l-1}^{OBJ/EXTREF} - y_l^{OBJ/EXTREF}}{h_{l-1}^{OBJ/EXTREF} * (\lambda_{l-1} - \lambda_l)} + \frac{y_l^{OBJ/EXTREF} - y_{l+1}^{OBJ/EXTREF}}{h_l^{OBJ/EXTREF} * (\lambda_l - \lambda_{l+1})}\right)$$

Secondly, the method knows the transfer function of the source of flashes of colours $f^{source}$ that gives the functions $S^{source}(\lambda)_l$ based on input parameters of the source of chrominance (R, G, B)$^{source}$ ($C^{source\ R/G/B}$ i) and the source of luminance BL$^{source}$ i=C$^{source\ BL}$ i. This transfer function is determined based on the "factory" theoretical output values of the electronic device and/or from a calibration done prior to the measurement. It is unuseful to necessarily redo this calibration prior to each measurement of colour. This transfer function is also available for devices with 4 and more primary colours (red-green-blue-white, red-green-blue-yellow, etc).

By way of Illustration, one form of the transfer function of the source is the following it being clarified that general consumer electronic devices usually seek to comply with the sRGB standard:

$f^{source}(C^{source\ R/G/B/BL}i)(\lambda) = S^{source}(\lambda)_i$
$f^{source}(C^{source\ R/G/B/BL}i)(\lambda) = C^{source\ BL}$ linéaire i*(S$^{source}(\lambda)_i^R$+S$^{source}(\lambda)_i^G$+S$^{source}(\lambda)_i^B$);
$C^{source\ BL}$ linéaire i=(a$^{source\ BL}$*C$^{source\ BL}$i+b$^{source\ BL})\gamma^{source\ BL}$+C$^{source\ BL}$
$S^{source}(\lambda)_i^{R/G/B} = C^{source\ R/G/B}$ linéaire i*S$^{source}(\lambda)^{R/G/B\ MAX}$
$C^{source\ R/G/B/BL}$ linéaire i=(a$^{source\ R/G/B}$*C$^{source\ R/G/B}$i+b$^{source\ R/G/B})\gamma^{source\ R/G/B}$+C$^{source\ R/G/B}$ Thirdly, the method knows the transfer function of the electronic colour image sensor $f^{capteur}$ that gives the chromaticity coordinates (X, Y, Z)$^{EC\_mesure}$ i in the colorimetric space of measurement of the luminous flux $E^{capteur}(\lambda)i$ entering in the sensor, as a function of its output parameters of chrominance (R, G, B)$^{capteur}$ i=(C$^{capteur\ R/G/B}$ i) and of luminance BV$^{capteur}$ i=(C$^{capteur\ BV}$ i). This transfer function is determined based on the "factory" theoretical output values of the electronic device and/or from a calibration done prior to the measurement. It is unuseful to necessarily redo this calibration prior to each measurement of colour.

By way of Illustration, one form of the transfer function of the electronic colour image sensor is the following it being clarified that general consumer electronic devices usually seek to comply with the sRGB standard:

Luminance Y: The method extracts from the EXIF the Brightness Value Bv$^{capteur}$ for calculating the luminance B$^{capteur}$ of the entering luminous flux (Bv=Log$_2$ (B/N/K) in cd/cm^2) with N=1/3.125 and K=10.7, then the method determines the luminance Y=K*B (K is a calibration parameter resulting from various losses: light scattering from the display screen, the absorption of the lens, etc).

Chrominance (x, y)$^{EC\_mesure}$: firstly, the method linearises the three (RGB)$^{capteur}$ coordinates with the use of a parametric function gamma (g, a, b) (f(x)=(a*x+b)^g) and it obtains the three (RGB_linéaire)$^{EC\_capteur}$ coordinates. Secondly, the method converts the 3 (RGB_linéaire)$^{EC\_capteur}$ coordinates into 3 (RGB_raw)$^{EC\_capteur}$ coordinates by multiplication with a 3×3 [WB$^{capteur}$] matrix which corresponds to the values of the white balance. The white balance consists of performing a chromatic adjustment to go from a D65 white (sRGB reference) to an estimated white. Thirdly, the method converts the 3 (RGB_raw)$^{EC\_capteur}$ coordinates into 3 (X, Y, Z)$^{EC\_capteur}$ coordinates by multiplication with the transition matrix 3×3 [p$^{EC\_capteur>EC\_mesure}$] which corresponds to a change in the vector base to get from the colorimetric space of the sensor to a vector subs pace which is the colorimetric measurement space. Fourthly, the method converts the three (X, Y, Z)$^{EC\_capteur}$ coordinates into (x, y)$^{EC\_capteur}$ coordinates.

Now developing the equations (E) by integrating them on the intersection of the spectra of the sensor and the source [$\lambda 1^{mesure}$; $\lambda 2^{mesure}$] (see FIG. 3) in order to generate the "Ei integrated" equations:

$$\int_{\lambda 1^{mesure}}^{\lambda 2^{mesure}} E^{capteur}(\lambda)_i * x/y/z^{EC\_mesure}(\lambda) * d\lambda =$$

$$\int_{\lambda 1^{mesure}}^{\lambda 2^{mesure}} (R^{OBJ}(\lambda) * S^{source}(\lambda)_i + I^{EXTREF}(\lambda)) * x/y/z^{EC\_mesure}(\lambda) * d\lambda$$

$f^{capteur}(C^{capteurR/G/B/BV}i)X/Y/Z^{EC\_mesure} =$ $$\int_{\lambda 1^{mesure}}^{\lambda 2^{mesure}} R^{OBJ}(\lambda) * f^{source} * (C^{sourceR/G/B/BL}i)(\lambda) * x/y/z^{EC\_mesure}(\lambda) *$$

$$d\lambda = + \int_{380\ nm}^{780\ nm} I^{EXTREF}(\lambda) * x/y/z^{EC\_mesure}(\lambda) * d\lambda$$

$f^{capteur}(C^{capteurR/G/B/BV}i)X/Y/Z^{EC\_mesure} =$ $$\int_{\lambda 1^{mesure}}^{\lambda 2^{mesure}} \left(\sum_{k=0}^{n^{OBJ}} y_k^{OBJ} * \Phi^{OBJ}(l, k, \lambda)\right) * f^{source} *$$

$$(C^{sourceR/G/B/BL}i)(\lambda) * x/y/z^{EC\_mesure}(\lambda) * d\lambda +$$

$$\int_{\lambda 1^{mesure}}^{\lambda 2^{mesure}} \left(\sum_{k=0}^{n^{EXTREF}} y_k^{EXTREF} * \Phi^{EXTREF}(l, k, \lambda)\right) *$$

-continued $$x/y/z^{EC\_mesure}(\lambda)*d\lambda$$

By interchanging the order of summations, the equations (Ei integrated) become:

$$f^{capteur}(C^{capteurR/G/B/BV}i)X/Y/Z^{EC\_mesure} =$$

-continued $$\sum_{k=0}^{n^{OBJ}} y_k^{OBJ} * \left( \int_{\lambda_{1mesure}}^{\lambda_{2mesure}} \Phi^{OBJ}(l,k,\lambda) * f^{source}(C^{sourceR/G/B/BL}i) \right.$$

$$\left. (\lambda)*x/y/z^{EC\_mesure}(\lambda)*d\lambda \right) + \sum_{k=0}^{n^{EXTREF}} y_k^{EXTREF} *$$

$$\left( \int_{\lambda_{1mesure}}^{\lambda_{2mesure}} \Phi^{EXTREF}(l,k,\lambda) * x/y/z^{EC\_mesure}(\lambda)*d\lambda \right)$$

$$f^{capteur}(C^{capteurR/G/B/BV}i)X/Y/Z^{EC\_mesure} =$$

$$\sum_{k=0}^{n^{OBJ}} y_k^{OBJ} * \left( \sum_{l=1}^{n^{OBJ}} \int_{\lambda_{l-1}}^{\lambda_l} \Phi^{OBJ}(l,k,\lambda) * f^{source}(C^{sourceR/G/B/BL}i) \right.$$

$$\left. (\lambda)*x/y/z^{EC\_mesure}(\lambda)*d\lambda \right) + \sum_{k=0}^{n^{EXTREF}} y_k^{EXTREF} *$$

$$\left( \sum_{k=0}^{n^{EXTREF}} \int_{\lambda_{l-1}}^{\lambda_l} \Phi^{EXTREF}(l,k,\lambda)*x/y/z^{EC\_mesure}(\lambda)*d\lambda \right)$$

Let's write $n^{OBJ+EXT\ REF} = (n^{OBJ}+1)+(n^{EXT}+1)$;
Let's write the vector $X^{OBJ+EXT\ REF}$ of dimension $n^{OBJ+EXT\ REF}$ such that: $(X^{OBJ+EXT\ REF})^T = (y^{OBJ}_0, \ldots, y^{OBJ}_{n^{OBJ}}, y^{EXT\ REF}_0, \ldots, y^{EXT\ REF}_{n^{EXT\ REF}})$; $(X^{OBJ+EXT\ REF})^T = X^{OBJ+EXT\ REF}_1, \ldots, X^{OBJ+EXT\ REF}_{n^{OBJ+EXT\ REF}}$);
Let's write the variables $\phi^{OBJ+EXT\ REF}(i,k^*, X/Y/Z^{EC\_mesure})$ such that:
if $1 \le k' \le n^{OBJ}+1$:

$$\Phi^{OBJ+EXTREF}(i,k',X/Y/Z^{EC\_mesure}) =$$

$$\sum_{l=1}^{n^{OBJ}} \int_{\lambda_{l-1}}^{\lambda_l} \Phi^{OBJ}(l,k,\lambda) * f^{source}(C^{sourceR/G/B/BL}i)$$

-continued $$(\lambda)*x/y/z^{EC\_mesure}(\lambda)*d\lambda$$

if $n^{OBJ}+2 \le k' \le n^{OBJ}+n^{EXT\ REF}+2$:

$$\Phi^{OBJ+EXT\ REF}(i,k',X/Y/Z^{EC\_mesure}) = \sum_{l=1}^{n^{EXT\ REF}} \int_{\lambda_{l-1}}^{\lambda_l} \Phi^{EXT\ REF}(l,k-n^{OBJ}-2,\lambda)*x/y/z^{EC\_mesure}(\lambda)*d\lambda$$

The equations (Ei integrated) may be written in the form of the following 3*N equations with the only unknowns being the $X^{OBJ+EXT\ REF}_k$:

$$f^{capteur}(C^{capteur\ R/G/B/BV}i)X/Y/Z^{EC\_mesure} = \sum_{k=1}^{n^{OBJ+EXT\ REF}} X_k^{OBJ+EXT\ REF} * \Phi^{OBJ+EXT\ REF}(i,k,X/Y/Z^{EC\_mesure});$$

Let's write the Jacobian matrix A of dimension (3*N, $n^{OBJ+EXT\ REF}$):

$$A = \begin{bmatrix} \Phi^{OER}(1,1,X) & \ldots & \Phi^{OER}(1,k',X) & \ldots & \Phi^{OER}(1,n^{OER},X) \\ \vdots & & \vdots & & \vdots \\ \Phi^{OER}(i,1,X) & \ldots & \Phi^{OER}(i,k',X) & \ldots & \Phi^{OER}(i,n^{OER},X) \\ \Phi^{OER}(i,1,Y) & \ldots & \Phi^{OER}(i,k',Y) & \ldots & \Phi^{OER}(i,n^{OER},Y) \\ \Phi^{OER}(i,1,Z) & \ldots & \Phi^{OER}(i,k',Z) & \ldots & \Phi^{OER}(i,n^{OER},Z) \\ \vdots & & & & \\ \Phi^{OER}(3*N,1,Z) & \ldots & \Phi^{OER}(3*N,k',Z) & \ldots & \Phi^{OER}(3*N,n^{OER},Z) \end{bmatrix}$$

Let the vector B equal to $f^{capteur}(C^{capteur\ R/V/B/BV}i)$ $X/Y/Z^{EC\_mesure}$ of dimension 3*N (i comprised between 1 and N).

The equations (Ei integrated) then form the linear system A*X=B.

The method will use the linear least squares algorithm for minimizing $\|A \cdot X - B\|_2$. The minimum is reached for: $Xmin = (A^T \cdot A)^{-1} \cdot A^T \cdot B$, hence the values of the interpolation points of $R^{OBJ}(\lambda)$ and $I^{EXT\ REF}(\lambda)$ and thus $I^{EXT}(\lambda) = R^{OBJ}(\lambda)/I^{EXT\ REF}(\lambda)$.

There are three conditions to be met: it is shown that the matrix $A^T \cdot A$ is invertible if and only if A is injective, which is true with $\Sigma_{l=1}^N S^{source}(\lambda)_i > 0$ over the interval $[\lambda 1^{mesure}; \lambda 2^{mesure}]$ and with $h = \max(\lambda_{k+1} - \lambda_k)$ sufficiently small. The mathematical demonstration is described in Annexe 2. In addition, $X^{OBJ+EXT\ REF}_k \ge 0$ for all the k because they are the ordinates of energy flow.

The first condition is satisfied by the construction of $[\lambda 1^{mesure}, \lambda 2^{mesure}]$ as the intersection of the source and sensor spectra (see FIG. 3) and the second, with a minimum of interpolation points for $R^{OBJ}(\lambda)$ and $I^{EXT}(\lambda)$.

As regards the third condition, the search to find Xmin is performed under the constraining condition $X^{OBJ+EXT\ REF}_k \ge 0$ for all the k, by using, among others, the NLLS (Non Linear Least Squares) algorithm of Lawson and Hanson (Jet Propulsion Laboratory of the National Aeronautics and Space Administration—NASA, Solving Least Squares Problems; SIAM Editions) or, more generally, a quadratic optimisation algorithm.

Note: The process is possible with other interpolation functions in linear or non-linear mode. The non-linear mode is also to be considered for moving from a system of 3*N equations based on the $X/Y/Z^{EC\_mesure}$ components to a system of N equations in the form of Euclidean type standards ($\| \ldots \|_2$) or of deltaE type of coordinates $(X, Y, Z)^{EC\_mesure}$.

Note: The method works on the one hand, with sensors that provide access to the coordinates (R,G,B_raw) and, on the other hand, with the sensors that do not provide access to the coordinates (R, G, B_raw), that do not provide access to the values of the white balance matrix, but provide the ability to lock the white balance values during the flashing process. In this second case, the values of the white balance matrix become additional unknowns to be determined (9 at the maximum). In order to solve this A'X=B system with increased white balance unknowns, the technique consists of increasing the number of flashes so as to have available an over-determined system, and then to solve either in the non-linear mode or in the linear iterative mode in the following manner (inter alia, when the possible values of parameters of the white balance are comprised within a finite set of discrete values): QR decomposition of the system with 2 blocks (X | White Balance), determination of X with the first block by developing a hypothesis with respect to the parameters of white balance, injection of values of X into the second block, determination of the parameters of white balance, and then reinjection into the first block in order to iterate X, and so on.

Two embodiments for viewing are possible for the invention in "colorimeter" mode in order to enrich the user experience and to improve the accuracy of the "colour chart" mode of the invention:
  First Embodiment: display screen 11 pointing in a direction away from the eyes of the user
  Second Embodiment: display screen 11 pointing in the direction of the eyes of the user First Embodiment: Display Screen Pointing in a Direction Away from the Eyes of the User The screen 11 displays a white figure on a black background (round/bands/square . . . ) so as to materialise the place to be viewed, then the user presses on the shutter release button normally used to take a photo (see button on the side for an iPhone S or at the bottom of the screen away from the position of the video conference camera).

A particular point of interest of this first embodiment is to be insensitive to the light environment which ensures the operation of the invention in virtually all the usual places, even those very brightly lit (interiors, exteriors). This quality is based on the very short distance between the target, the screen 11 and the image sensor 12, on the high brightness of the field emission display screens and on the fact that there are several "barriers" indeed serving as blocks to the surrounding light rays: the support for the display screen and the image sensor, hand/finger(s) of the user on the sides.

Second Embodiment: Display Screen Pointing in the Direction of the Eyes of the User The display screen 11 is placed facing towards the external illuminant, typically facing the sky. The user then comes to place on the top of the screen the coloured object to be measured (part close to the image sensor). In order to facilitate the manoeuvre, the screen 11 is divided into two parts, the upper part close to the image sensor 12 is used to emit the luminous flux for the measurement, the lower part serves to provide a feedback loop to the user on the place that is pointed (wysiwyg).

A particular point of interest of this second embodiment is the ability to measure the reflectance of the screen $R^{ecran}$ ($\lambda$).

The device 10 according to the present invention makes it possible to transform into a spectrometer any electronic equipment unit having a field emission display screen 11 and an image sensor 12 located on the side, including amongst others, phones, tablets, PDAs (personal digital assistants), computers and monitors/TVs equipped with a video conferencing camera. It is also intended for example for cameras and camcorders having a swivel/removable screen.

The device 10 according to the present invention offers the possibility of opening up new avenues for mobile or hand held uses for accurate measurement of absolute colour in a daily context, without requiring a dedicated device. The following list is not exhaustive:
  the measurement of colours on objects of all kinds: materials, liquids, gases, paints, paintings, tapestries, graphics, textiles, plastics, wood, metals, soils, minerals, plants and foods, etc;
  the use of colour bar codes (in one or more dimensions);
  the measurement of colours, for medical or cosmetic purposes with respect to humans and living beings/organisms: skin, pimples, moles, hair, fur/hair coat, makeup, teeth, etc;
  the measurement of colours with a view to assisting people having colour blindness and/or who are blind;
  the measurement of the colour of object(s) appearing in a photograph in order to make chromatic adjustments and guide the white balance algorithm instead of using a supplementary colour chart of calibrated colours.

The invention is described in the foregoing sections solely by way of example. It is understood that the person skilled in the art is capable of developing different variants of the invention without however in any way departing from the scope of the patent.

Annexe 1: Flashing Algorithm

Introduction

The present annexe defines a flashing algorithm that is aimed at optimising the conditioning of the matrix A by seeking to exclude to the maximum possible degree the said flashes and to distribute them in as homogeneous a manner as possible in the colorimetric measurement space, while remaining within the gamuts of the source and the electronic image sensor and while also ensuring that the exterior illuminant remains constant during flashes.

Description of the Flashing Algorithm

The said algorithm takes as input a number of required valid flashes N.

The said algorithm returns as output a sequence of N valid flashes (with for each flash, the input parameters of the source and the output parameters of the sensor. The index of this sequence of flashes is denoted as i (flash_i).

The said algorithm interacts with the method and the device according to the invention that emit flashes of colours towards a target object and that capture the reflected light with an electronic image sensor (including among others, a smartphone with the screen that emits flashes and the video conferencing camera which captures light reflected by the target object).

The said algorithm works in the presence of an external illuminant $I^{ext}(\lambda)$.

The algorithm is broken down into 4 main "phases", and each phase into "steps":
  Phase 1: emission of a flash "black 1"
  Phase 2: finding the 3 vertices that maximise the "flashing triangle"
  Phase 3: homogeneous completion of the number of required valid flashes
  Phase 4: emission of a flash "black 2"

Notation: In the sections that follow, the coordinates (dispR %, dispG %, dispB %) denote the chrominance input parameters of the source of the flashes of colours as a percentage ([0, 1]). DispBL % denotes the luminance input parameter of the source of the flashes of colours as a percentage ([0;1]). In practice, they are binary values, generally ranging between 0 and 255 (dispECMY, dispECMx, dispECMy) denote the coordinates of the luminous flux emitted by the source in the colourimétrique space $Yxy^{EC\_mesure}$.

Notation: In the sections that follow, the coordinates (camR %_k, camG %_k, camB %_k) denote the chrominance output parameters of the electronic image sensor as a percentage ([0;1]). In practice, they are binary values, generally ranging between 0 and 255. camBv denotes the Brightness Value which is the luminance output parameter of the electronic image sensor (see standard EXIF). (camECMX, camECMY, camECMZ) and (camECMY, camECMx, camECMy) denote the coordinates of the luminous flux emitted by the source respectively in the colorimetric space $XYZ^{EC\_mesure}$ and in the chromaticity diagram thereof.

Notation: In the sections that follow, the values dispEps and camEps signify that the values of the threshold below which the input values of the source and the output values of the sensor shall be considered to be nil.

Phase 1: Emission of a Flash "black 1"

The objective of Phase 1 is twofold: to check whether the external illuminant is compatible with the physical limitations of the device and to check to ensure that external illuminant is constant during the flashing.

The algorithm outputs a "black" flash, that is to say, it performs a measurement with the source switched off, that is dispR %=dispG %=dispB %=0 (and dispBL=0 if possible).

The algorithm is faced with two possible cases:
  Case 1: The value camECMY is strictly higher than a limit camECMY_IEmax defined as a function of the maximum luminance of the source of the flashes of colours, which signifies that the luminance of the external illuminant is too strong compared to the physical limitations of the source of the flashes of colours. The measurement is not possible. The algorithm interrupts the flashing process by generating an error code;
  Case 2: The value camECMY is less than or equal to a limit camECMY_IEmax defined as a function of the maximum luminance of the source of the flashes of colours, which signifies that the luminance of the external illuminant is compatible with the physical limitations of the source of the flashes of colours. The algorithm stores in the memory the values of chrominance and luminance measured by the colour image sensor in order to ensure that the illuminant remains constant during the flashing, and then the algorithm proceeds to step 1 of the phase 2.

Note: In this present Annexe 1, there is mention of only two black flashes for checking the constancy of the external illuminant, a first one at the beginning of the flashing and a second one at the end. Depending on the conditions of use of the device according to the invention, it is quite possible to reduce or increase the number of black flashes to check the constancy of the external illuminant.

Phase 2: Finding the 3 Vertices that Maximise the "Flashing Triangle"

The objective of Phase 2 is to build a "flashing sub-gamut" of maximum size for a given precision, while remaining compatible with the colour gamut of the source of light flashes and that of the electronic image sensor.

Let's define the function f: (dispECMx, dispECMy)→(camECMx, camECMy) of the gamut of the source of the flashes of colours to the gamut of electronic image sensor.

The "source-sensor sub-gamut" is defined as being the intersection of the gamut of the sensor and the image by f of the gamut of the source. The source sub-gamut is defined as being the inverse image by f of the sensor sub-gamut.

In other words, the objective of Phase 2 is to determine a triangle included in the "sensor-source sub-gamut" of maximum size for a given precision. This triangle is called "flashing triangle".

Step 1: Finding a Pivot

The purpose of Step 1 is to define a flash pivot within the sensor gamut.

The algorithm goes to step 1.1 by using a pre-defined flash pivot value for the iteration k=1, for example a white flash of maximum luminance (dispR %_1=dispG %_1=dispB %_1=dispBL %_1=1).

Step 1.1: Testing of a Flash Pivot of Index k

The purpose of step 1.1 is to test whether the proposed flash pivot of index k is within the sensor gamut.

The algorithm asks the source to generate the flash pivot k and it retrieves the output coordinates of the sensor (camR %_k, camG %_k, camB %_k, camBv_k).

The algorithm is faced with two possible cases:
  Case 1.1-1: At least one of the components (camR %_k, camG %_k, camB %_k) is less than or equal to camEps, which signifies that the flash is outside the gamut of the sensor. The algorithm proceeds to step #1.2
  Case 1.1-2: All the components (camR %_k, camG %_k, camB %_k) are strictly greater than camEps, which signifies that the flash is within the gamut of the sensor. The algorithm goes to Step 2.

Step 1.2: Generation of a New Flash-Pivot of Index k+1

The purpose of Step 1.2 is to generate a new flash pivot of index k+1 that is within the sensor gamut unlike the previous flash pivot of index k.

The algorithm is faced with two possible cases depending upon (camR %_k, camG %_k, camB %_k)
  Case 1.2-1: Only one of the three components (camR %_k, camG %_k, camB %_k) is zero with the flash pivot of index k. The algorithm will then try a new flash pivot (k+1) with a greater proportion of the component that is cancelled. By way of an illustration, if camR %_k<camEps:

$$dispR\%_{k+1} = \alpha * dispR\%_k$$

$$dispG\%_{k+1} = dispG\%_k * \frac{1 - \alpha * dispR\%_k}{dispG\%_k + dispB\%_k}$$

$$dispB\%_{k+1} = dispB\%_k * \frac{1 - \alpha * dispR\%_k}{dispG\%_k + dispB\%_k}$$

$$\text{with } 1 < \alpha < \frac{1}{dispR\%_k}$$

The algorithm proceeds to step 1.1 with this flash pivot k+1
  Case 1.2-2: Two of the three components are zero (camR %_k, camG %_k, camB %_k). The algorithm will then try a new flash pivot (k+1) with a higher proportion of both the two components that were cancelled. By way of an illustration, if camR %_k<camEps and camG %_k<camEps.

$$dispR\%_{k+1} = \alpha * dispR\%_k$$

$$dispG\%_{k+1} = \beta * dispG\%_k$$

$$dispB\%_{k+1} = 1 - \alpha * dispR\%_k - \beta * dispG\%_k$$

with $\alpha > 1$, $\beta > 1$ et $\alpha * dispR\%_k + \beta * dispG\%_k < 1$

The algorithm goes to step 1.1 with this flash pivot k+1.

Case 1.2-3: the algorithm is unable to find a new flash pivot k+1. Then the algorithm declares the impossibility of performing the measurement and exits the algorithm by returning an error code.

Step 2: Shortcut for Going from the Flash Pivot to a First Flashing Triangle of a Lane Size The purpose of Step 2 is to save on flashes so as to cause the increase in size of the flashing triangle around the flash pivot.

To do this, the algorithm has available a database with the input of the input and output values of reference flashes and with the outputting of the coordinates of the associated flash triangles. This database is thus a shortcut for causing the flashing triangle to grow.

More specifically, the algorithm frames the flash pivot with the 3 closest reference flashes (in the sense of a Euclidean norm in the measurement space). Then it mixes the coordinates of the reference flashing triangles by using the barycentric coordinates of the flash pivot in the triangle of the 3 reference flashes. The algorithm thus obtains a flashing triangle of large size around the flash pivot. It then performs a homothetic transformation or homogeneous dilation of ratio K<1 on this triangle with respect to the flash pivot so as to take a safety margin and it asks the source to emit the 3 flashes of colour corresponding to the three vertices of the said triangle. The algorithm then goes to the step 4.1 for analysing the results.

If the algorithm is not able to frame the flash pivot with 3 reference flashes, it selects the closest reference flash from the database (if this latter is sufficiently close in relation to an adjustable threshold) then it causes the 3 flashes to be emitted as before and it goes to the step 4.

If there is no reference flash sufficiently close in the database, the algorithm proceeds to step 3.

Step 3: Passage from the Flash Pivot to a First Flashing Triangle of Small Size

The purpose of the Step 3 is to create a first flashing triangle of small size by using three points, the first being the sensor output for the flash pivot (camR %_k, camG %_k, camB %_k).

The algorithm orders the values (camR %_k, camG %_k, camB %_k), and then generates two new flashes, the first having more (in proportion) of the lowest component, the second having more of the two lowest components.

By way of illustration, if camG %_k<camR %_k<camB %_k, the algorithm outputs a first flash having more (in proportion) of the green component, and then a second flash having more of the green component and more of the red component.

Step 3.1: Testing of the Flashing Triangle of Small Size

The purpose of step 3.1 is to test whether the small sized flashing triangle is included in the sensor gamut.

The algorithm is faced with 3 possible cases:

Case 3.1-1: at least one flash exits out of the sensor gamut. The algorithm proceeds to step 3.2.

Case 3.1-2: the sensor outputs for these flashes are aligned with the sensor output for the flash pivot. The algorithm declares the impossibility of performing the measurement and exits the algorithm by returning an error code.

Case 3.1-3: the small sized flashing triangle is included in the sensor gamut and the points are not aligned. The algorithm proceeds to the step 4.

Step 3.2: Generation of a New Flashing Triangle of Small Size

The purpose of step 3.2 is to generate a new small sized flashing triangle by replacing the flashes whose sensor output has exited out of the sensor gamut.

The algorithm replaces the flash or flashes that have failed by adding less of the components added. The algorithm proceeds to step 3.1 with this new base.

Step 4: Maximisation of the Size of the Flashing Triangle

The purpose of step 4 is to construct the flashing triangle of the maximum size for a given precision.

The transformation f is assumed to be linear and the algorithm determines this transformation by using the data from the three points of the base of the sensor gamut. The algorithm infers therefrom the source-sensor sub-gamut and then determines the flashing triangle with maximum surface area included in this sub-gamut. It then performs a homothetic transformation or homogeneous dilation of ratio K<1 on this triangle with respect to the flash pivot so as to take a safety margin and it asks the source to emit the 3 flashes of colour corresponding to the three vertices of the said triangle. The algorithm then goes to the step 4.1 for analysing the results.

Step 4.1: Testing of a Flashing Triangle of Order k

The purpose of step 4.1 is to test whether the flashing triangle is included in the sensor gamut.

The algorithm is faced with two possible cases:

Case 4.1-1: a vertex of the flashing triangle exits out of the sensor gamut. The algorithm proceeds to step 4.2.

Case 4.1-2: the flashing triangle is considered to be not sufficiently large, because at least one of its vertices is too far from the vertex of the closest sensor gamut (in the sense of the Euclidean norm within the measurement space), and the flash corresponding to this vertex is also too far from the vertex of the closest source gamut. The algorithm proceeds to the step 4.3.

Case 4.1-3: the flashing triangle is satisfactory. The algorithm proceeds to the Phase 3.

Step 4.2: Generation of a New Vertex of Index k+1 of the Flashing Triangle Following the Exit from the Sensor Gamut of the Vertex of Index k The purpose of step 4.2 is to generate a new vertex of index k+1 of the flashing triangle within the sensor gamut unlike the vertex of index k and with coordinates (camR %_k, camG %_k, camB %_k).

The algorithm is faced with two possible cases depending upon (camR %_k, camG %_k, camB %_k):

Case 4.2-1: Only one of the three components (camR %_k, camG %_k, camB %_k) is zero. The algorithm will then try a new flash pivot (k+1) with a greater proportion of the component that is cancelled. By way of an illustration, if camR %_k<camEps, $$dispR\%_{k+1} = \alpha * dispR\%_k$$

$$dispG\%_{k+1} = dispG\%_k * \frac{1 - \alpha * dispR\%_k}{dispG\%_k + dispB\%_k}$$

$$dispB\%_{k+1} = dispB\%_k * \frac{1 - \alpha * dispR\%_k}{dispG\%_k + dispB\%_k}$$

$$avec 1 < \alpha < \frac{1}{dispR\%_k}$$

The algorithm proceeds to the step 1.1 with this flash pivot of k+1.

Case 4.2-2: Two of the three components are zero (camR %_k, camG %_k, camB %_k). The algorithm will then try a new flash pivot (k+1) with a higher proportion of both the two components that were cancelled. By way of an illustration, if camR %_k<camEps and camG %_k<camEps, dispR %_k+1=*dispRα %_k, $$dispR\%_{k+1} = \alpha * dispR\%_k$$
$$dispG\%_{k+1} = \beta * dispG\%_k$$
$$dispB\%_{k+1} = 1 - \alpha * dispR\%_k - \beta * dispG\%_k$$
$$aveca > 1, \beta > 1 et \alpha * dispR\%_k + \beta * dispG\%_k < 1$$

The algorithm proceeds to the step 1.1 with this flash pivot k+1.

Case 4.2-3: the algorithm is unable to find a new flash pivot k+1. Then the algorithm declares the impossibility of performing the measurement and exits the algorithm by returning an error code.

Step 4.3: Generation of a New Vertex for the Flashing Triangle Because of the Insufficient Size of the Flashing Triangle The purpose of step 4.3 is to enlarge the flashing triangle because at least one of its vertices is too far from the vertex of the closest sensor gamut and the flash flash_k_1 corresponding to this vertex is also too far from the vertex of the closest source gamut.

To be noted are flash_k_2 and flash_k_3 the two flashes whose sensor outputs are the other two vertices of the flashing triangle.

The algorithm generates two flashes respectively barycentre of the system {(flash flash_k_1, a), (flash flash_k_2, 1−α)} and barycentre of the system {(flash flash_k_1, α), (flash flash_k_3, 1−α)} (for example: α=0.2). These two flashes and the flash flash_k_1 form a triangle on which the transformation f is assumed affine. The algorithm determines this transformation by using the data from the three points and infers therefrom the source-sensor sub-gamut and then determines the vertex that provides the ability to obtain the flashing triangle with maximum surface area included in this sub-gamut. It then performs a homothetic transformation or homogeneous dilation of ratio K<1 on this point with respect to the preceding vertex so as to take a safety margin and it asks the source to emit the flash of colour corresponding to the said point. If the sensor output exits out of the sensor gamut, the algorithm repeats the operation with a higher margin (smaller K), otherwise the sensor output replaces the preceding vertex and forms along with the other vertices a new flashing triangle. The algorithm proceeds to the step 4.1 with this new flashing triangle.

Phase 3: Homogeneous Completion of the Number of Valid Flashes Required

The objective of Phase 3 is to generate a sequence of N flashes whose sensor outputs are distributed in a homogenous manner within the flashing triangle defined during the Phase 2.

The algorithm thus has available the coordinates of the vertices of the flashing triangle as well as a certain number of intermediate flashes that were used to determine the flashing triangle during the phase 2 (at least one: the flash pivot). These points are denoted as (camECMx_k, camECMy_k).

Step 1: Generation of a Grid of N Points in the Flashing Triangle

The purpose of step 1 is to generate a grid of N points distributed in a homogeneous manner within the flashing triangle.

The algorithm generates a grid of N points distributed as described in FIGS. 4 to 8, for values of N ranging from 1 to 15.

The algorithm proceeds to the Step 2 with this grid of N points within the flashing triangle, denoted as (camECMx_g_k, camECMy_g_k).

Step 2: Generation of a Flash

The purpose of this step 2 is to generate flashes whose sensor output approximates ideal points located on the grid defined during the step 1.

For each point (camECMx_g_k, camECMy_g_k), the algorithm determines the triangle with vertices of three unaligned points(camECMx_k, camECMy_k) which minimizes the sum of squares of the distances from the point (camECMx_g_k, camECMy_g_k) to the vertices of the triangle. This sum is referred to as the distance to the triangle.

The algorithm chooses the point (camECMx_g_k, camECMy_g_k) whose distance to the triangle is the smallest.

The transformation f is assumed to be linear on this triangle and its neighbouring triangles, and it is determined using the data from the 3 vertices of the triangle. The algorithm thus determines the flash (dispECMx_g_k, dispECMy_g_k) the sensor output of which will be (camECMx_g_k, camECMy_g_k).

If the sensor output for the flash (dispECMx_g_k, dispECMy_g_k) exits out of the sensor gamut, the flash is not retained.

The point (camECMx_g_k, camECMy_g_k) is removed from the list of points to be brought close.

The algorithm is faced with two possible cases:

Case 2-1: there no longer remain any points (camECMx_g_k, camECMy_g_k) to be brought close. The algorithm proceeds to the step #3 with the set of flashes which have been generated over the course of phases 2 and 3.

Case 2-2: there still remains at least one point (camECMx_g_k, camECMy_g_k) to be brought close. The algorithm proceeds to the step 2 with the new list of points (camECMx_g_k, camECMy_g_k).

Step 3: Selection of Flashes to be Returned

The algorithm selects only the flashes whose sensor output is sufficiently close to a point of the grid generated in step 1 (in the sense of the Euclidean distance in the colorimetric space of measurement). If two points are sufficiently close to a point in the grid, then only the closest point is selected. The algorithm then passes on to the phase 4.

Note: if at least one flash whose sensor output is strictly included within the sensor gamut is selected, then the condition $\Sigma_i$ $(i=1)^T N \equiv (S^{source}(\lambda)_i) > 0$ over the interval $[\lambda 1^{mesure}; \lambda 2^{mesure}]$ used in the demonstration of the invertibility of $A^T * A$ in Annexe 2 is satisfied.

Phase 4: Emission of a Flash "black 2"

The objective of this Phase 4 is to check to ensure that external illuminant is constant during the flashing.

The algorithm outputs a "black" flash, that is to say that it proceeds to perform a measurement with the source switched off, that is dispR %=dispG %=dispB %=0 (and dispBL=0 if possible).

The algorithm is faced with two possible cases:

Case 1: The difference between the values of chrominance and luminance measured by the colour image sensor between the current black flash and the preceding black flash is strictly greater than a given threshold. This signifies that external illuminant has changed over the course of the flashes. The algorithm interrupts the flashing process by generating an error code;

Case 2: The difference between the values of chrominance and luminance measured by the colour image sensor between the current black flash and the preceding black flash is less than or equal to a given threshold. This signifies that external illuminant has not changed over the course of the flashes and thus that the flash process is valid. The algorithm returns the sequence of N valid flashes created with for each flash, the input parameters of the source and the output parameters of the sensor.

Appendix 2: Demonstration of the Invertibility of $A^{T}*A$

It is shown that $A^{T}*A$ is invertible in the case where $\Sigma_{i=1}^{N} S^{source}(\lambda)_i > 0$ over the interval $[\lambda 1^{mesure}; \lambda 2^{mesure}]$ (the flashes cover all of the wavelengths considered for determining $R^{OBJ}(\lambda)$ and $I^{ext}(\lambda)$), and for $h = \max(\lambda_{i+1} - \lambda_i)$ that is sufficiently small.

Let x be an eigen vector associated with the eigen value µ

There is on the one hand $(A^{T}*A \cdot x, x) = (\mu \cdot x, x) = \mu \cdot (x, x) = \mu \|x\|^2$ And on the other hand $(A^{T}*A \cdot x, x) = (A \cdot x, A \cdot x) = \|A \cdot x\|^2$ Thus $\mu = \|A \cdot x\|^2 / \|x\|^2$ Thus µ is positive and it is so strictly if A is injective.

Thus if A is injective, all the eigen values of $A^{T}*A$ are strictly positive, therefore $A^{T}*A$ is invertible.

Conversely, if A is not injective, there exists non zero x such that $A \cdot x = 0$. Thus one then gets $A^{T}*Ax = 0$ therefore $A^{T}*A$ is not invertible.

Finally, $A^{T}*A$ is invertible if and only if A is injective.

Lemma 1: The Integral of a Sealed Cubic Spline $S(\lambda)$ with Zero Slopes at the Ends $[S(\lambda)*d\lambda$ is Always Positive when all the $y_i$ are Positive Case No 1: If all the $y_i = 0$, Then $s(\lambda) = 0$ for all the λ due to the zero slopes at the edges, hence $Int\{S(\lambda)*d\lambda\} = 0$ Case 2: If there Exists One y>0 and if all the Other $y_i$ are Zero:

y_i creates a "positive belly" over $[\lambda_{i-1}; \lambda_i] \cup [\lambda_i; \lambda_{i+1}]$ (area >0) and "negative bellies" over $[\lambda_{i-2}; \lambda_{i-1}]$ and $[\lambda_{i+1}; \lambda_{i+2}]$ (area <0), and so on up to the edges. As the spline function minimizes the energy of the tongue, the surface area of the positive belly $[\lambda_{i-1}; \lambda_i] \cup [\lambda_i; \lambda_{i+1}]$ is greater than those of the negative bellies $[\lambda_{i-2}; \lambda_{i-1}]$ and $[\lambda_{i+1}; \lambda_{i+2}]$. This is due to the fact that $|p_{i+1}| > |p_{i+2}| > \ldots > |p_n| = 0$ and $|p_{i-1}| > |p_{i-2}| > \ldots > |p_0| = 0$. As a result, the surface area of the positive bellies is greater than the negative bellies and therefore $\int S(\lambda)*d\lambda > 0$ Case 3: If there Exist Two $y_i > 0$:

Case no 3.1: $y_i$ and $y_{i+1} > 0$ (contiguous): This creates a "large" positive belly. The reasoning given for the case no 2 is applicable.

Case no 3.2: $y_i$ and $y_{i+2} > 0$ ($y_{i+1} = 0$): there are 2 positive contiguous bellies. The reasoning given for the case no 2 is applicable.

Case no 3.3: $y_i$ and $y_{i+3} > 0$ ($y_{i+1} = y_{i+2}$): there is 1 positive belly, 1 negative belly, 1 positive belly. The reasoning given for the case no 2 is applicable.

Case no 3.4: $y_i$ and $y_{i+k} > 0$ with k>3. Same as previously given for Case no 3.3.

Case 4: If there Exist at Least 3 $y_i > 0$ (General Case)

Thus the reasoning given for the cases under Case no 3 is applicable. QED

Lemma 2: The Integral of a Sealed Cubic Spline $S(\lambda)$ with Zero Slopes at the Ends Multiplied by a Function $K(\lambda) > 0$ ($[S(\lambda)*K(\lambda)*d\lambda$ is Always Positive when all the $y_i$ are Positive Lemma 1 (case no 2) is not directly applicable because the term $K(\lambda)$ can greatly reduce the area of the positive bellies and increase that of the negative bellies.

The trick is to increase the number of interpolation points in order to reduce the surface area of the negative bellies.

Let us be positioned in the scenario of case no 2 of the Lemma 1. The error of a sealed spline is bounded by the following formula: $|f(x)-s(x)| \leq a*h^4$ with $a = 5/384*\max[a; b]\{|f(4)(E)|\} > 0$ (constant value), and $h = \max\{|x_i - x_{i-1}|\}$.

That is to say that: $f(x) - a*h \leq s(x) \leq f(x) + a*h$

Since $f(x) \geq 0$ ($R^{OBJ}(\lambda)$ and $I^{EXT}(\lambda)$ are the energy flows), $s(x) \geq -a*h$, thus the maximum surface area of the negative bellies $[\lambda_{i-2}; \lambda_{i-1}] \cup [_{i+2}]$ is equal to $-2*a*h^2$.

The surface area of the positive bellies remains constant because the increase in the number of interpolation points will create multiple contiguous $y_i > 0$.

As a consequence, there is an h for which the surface area of the positive bellies is strictly greater than that of the negative bellies.

Returning to the Demonstration

Let x be such that $A*x = 0$ with x formed of the ordinates of the sealed cubic spline with zero slopes at the ends representing $R^{OBJ}(\lambda)$ and $I^{ext}(\lambda)$.

Showing that x=0

We get for all $i = 1, \ldots, N$ and for any sensitivity $x/y/z(\lambda)$:

$\int R^{OBJ}(\lambda)*S^{source}(\lambda)_i*x/y/z(\lambda)*d\lambda + \int I^{ext}(\lambda)*x/y/z(\lambda)*d\lambda = 0$ where $R^{OBJ}(\lambda)$ and $I^{ext}(\lambda)$ are the sealed cubic spline functions with zero slopes at the ends.

Summing for the $3*N$ equations, we obtain:

$$\int R^{OBJ}(\lambda) * \sum_{i=1}^{N} S^{source}(\lambda)_i * (x(\lambda) + y(\lambda) + z(\lambda)) * d\lambda +$$

$$\int I^{ext}(\lambda) * (x(\lambda) + y(\lambda) + z(\lambda)) * d\lambda = 0$$

With $x(\lambda) + y(\lambda) + z(\lambda) > 0$ and $\Sigma_{i=1}^{N} S^{source}(\lambda)_i > 0$ for all λ, it is deduced from Lemma 2 that there exists a sufficiently small h such that:

$$\int R^{OBJ}(\lambda) * \sum_{i=1}^{N} S^{source}(\lambda)_i * (x(\lambda) + y(\lambda) + z(\lambda)) * d\lambda = 0$$

and $\int I^{ext}(\lambda)*(x(\lambda)+y(\lambda)+z(\lambda))*d\lambda = 0$

Since $R^{OBJ}(\lambda) = 0$ and $I^{ext}(\lambda) = 0$ for all λ, ie x=0. A is injective. Therefore $A^{T}*A$ is invertible. QED

The invention claimed is:

1. A method for measuring the uniform diffuse reflectance $R^{OBJ}(\lambda)$ at least at one point of an object (30) by using a device (10) comprising a means (11) capable of emitting coloured illuminants expressed in the form of luminous flux and an electronic colour image sensor (12), characterized in that it comprises the following steps:

placing of the said object (30) in a zone located opposite and substantially perpendicular to the said means (11) capable of emitting coloured illuminants in the form of luminous fluxes of colours and located in the field of vision of the said electronic colour image sensor (12), the said object (30) also being subjected to an external illuminant in the form of a constant and unknown surrounding external luminous flux (40) $I^{ext}(\lambda)$, where $\lambda$ denotes the wavelength; emission by the said means (11) of a series of N illuminants $S^{source}(\lambda)_i$ (with N being a natural number greater than one, i varying from 1 to N and $\lambda$ being the wavelength), $S^{source}(\lambda)_i$ being known as a function of the input parameters of the said means (11) capable of emitting luminous fluxes of colours, capture by the said electronic colour image sensor (12) of the luminous flux reflected at least at one point of the said object (30) and entering in the sensor, the said luminous flux being denoted as $E^{capteur}(\lambda)_i$, with N being a natural number strictly greater than two, i varying from 1 to N and $\lambda$ being the wavelength; and obtaining of N equations "$E_i$": $E^{capteur}(\lambda)_i = R^{OBJ}(\lambda) * (I^{ext}(\lambda) + S^{source}(\lambda)_i)$ due to the additive nature of the wave light and by definition of the uniform diffuse reflectance $R^{OBJ}(\lambda)$ at least at one point of the object (30); and determination by the said device (10) of the two unknown continuous functions $R^{OBJ}(\lambda)$ and $I^{ext}(\lambda)$ by solving the system of N equations $E_i$:

by integrating each equation $E_i$ on the intersection of the source and sensor spectra, by denoting x, y and z the sensitivities in the colorimetric base selected, each equation $E_i$ then generating three "$E_i$ integrated" equations:

$$\int E^{capteur}(\lambda)_i * x(\lambda) * d\lambda = \int R^{OBJ}(\lambda) * (I^{ext}(\lambda) + S^{SOURCE}(\lambda)_i) * x(\lambda) * d\lambda$$

$$\int E^{capteur}(\lambda)_i * y(\lambda) * d\lambda = \int R^{OBJ}(\lambda) * (I^{ext}(\lambda) + S^{SOURCE}(\lambda)_i) * x(\lambda) * d\lambda$$

$$\int E^{capteur}(\lambda)_i * z(\lambda) * d\lambda = \int R^{OBJ}(\lambda) * (I^{ext}(\lambda) + S^{SOURCE}(\lambda)_i) * x(\lambda) * d\lambda$$

by calculating the numerical value corresponding to the left-hand side of the Ei integrated equations with the use of the output parameters of the digital image sensor; and by expressing the two unknown continuous functions $R^{OBJ}(\lambda)$ and $I^{ext}(\lambda)$ with the use of a finite number of interpolation points $(\lambda_j, y_j)$ connected by at least one interpolation function $s(\lambda)$ for maintaining the continuous nature of the said unknown continuous functions $R^{OBJ}(\lambda)$ and $I^{ext}(\lambda)$, the $\lambda_j$ being wavelengths selected in the intersection of the source and sensor spectra and being input parameters of the method, chosen to minimize the number of interpolation points for a given precision; and by finding the parameters $y_j$ of the functions $R^{OBJ}(\lambda)$ and $I^{ext}(\lambda)$ that minimize the least squares system $\|A*X-B\|_2$ resulting from the $E_i$ integrated equations.

2. A method according to claim 1, characterized in that it further includes a step of determining the value of the external illuminant $I^{ext}(\lambda)$.

3. A method according to claim 1, characterized in that it includes in addition, a step of transcription of the function $R^{OBJ}(\lambda)$ of uniform diffuse reflectance at least at one point of the object (30) into the CIE XYZ coordinates for a given illuminant.

4. A method according to claim 1, characterized in that the series of N illuminants is of the same order of magnitude as the number of interpolation points for determining the values of the uniform diffuse reflectance $R^{OBJ}(\lambda)$ at least at one point of the object (30) and of the external illuminant $I^{ext}(\lambda)$.

5. A method according to claim 1, characterized in that it includes a step of determining the values of the uniform diffuse reflectance $R^{OBJ}(\lambda)$ at least at one point of the object (30) and the external illuminant $I^{ext}(\lambda)$ in several spectral bands.

6. A method according to claim 1, characterised in that the said device (10) makes use of a screen for emitting flashes of colour and an electronic image sensor for sensing and capturing the light reflected by the target object.

7. A method according to claim 1, characterised in that the said device (10) is a camera unit or a camera with in built or removable flash.

8. A method according to claim 1, characterized in that the said device (10) implements waveguides for ensuring effective transiting of the emission and reception of flashes of colours.

9. A method according to claim 1, characterized in that it is implemented in order to take spectrometric photographs of objects and to make chromatic adjustments (balancing of whites) at will.

10. A method according to claim 1, characterized in that it is implemented in order to measure the colour of an element included in the following group: materials, solids, liquids, gases, paintings, tapestries, graphics, textiles, plastics, woods, metals, soils, minerals, plants and foods.

11. A method according to claim 1, characterized in that it is implemented for the measurement of colours for medical or cosmetic purposes on human beings and living organisms of at least one element included in the following group: skin, pimples, moles, hair, fur, makeup, and teeth.

12. A method according to claim 1, characterized in that it is implemented for the use of colour barcodes, of one or more dimensions.

13. A method according to claim 1, characterized in that it is implemented with a view to assisting people having colour blindness and/or who are blind.

14. A device (10) comprising the means (11) capable of emitting colour illuminants in the form of luminous flux of colours and an electronic colour image sensor (12), for measuring the uniform diffuse reflectance $R^{OBJ}(\lambda)$ at least at one point of an object (30) placed in a zone located opposite and substantially perpendicular to the said means (11) capable of emitting colours and located in the field of vision of the said electronic colour image sensor (12), and also being subjected to an external illuminant in the form of a constant and unknown surrounding external luminous flux (40) denoted as $I^{ext}(\lambda)$, characterized in that it comprises the means for:

emitting a series of N illuminants $S^{source}(\lambda)_i$ (with N being a natural number strictly greater than two, i varying from 1 to N and $\lambda$ being the wavelength), $S^{source}(\lambda)_i$ being known as a function of the input parameters of the said means (11) capable of emitting luminous fluxes of colours, capture by the said electronic colour image sensor (12) of the luminous flux reflected at least at one point of the said object (30) and entering in the sensor, the said luminous flux being denoted as $E^{capteur}(\lambda)_i$, with N being a natural number greater than one, i varying from 1 to N and $\lambda$ being the wavelength; and obtaining of N equations ($E_i$): $E^{capteur}(\lambda)_i = R^{OBJ}(\lambda) * (I^{ext}(\lambda) + S^{source}(\lambda)_i)$ due to the additive nature of the wave light and by definition of the uniform diffuse reflectance $R^{OBJ}(\lambda)$ at least at one point of the object (30); and determining the two unknown continuous functions $R^{OBJ}(\lambda)$ and $I^{ext}(\lambda)$ by solving the system of N equations $E_1$: by integrating each equation $E_i$ on the intersection of the source and sensor spectra, by denoting x, y and z the sensitivities in the colorimetric base selected, each equation $E_i$ then generating three "$E_i$ integrated" equations:

$$\int E^{capteur}(\lambda)_i * x(\lambda) * d\lambda = \int R^{OBJ}(\lambda) * (I^{ext}(\lambda) + S^{SOURCE}(\lambda)_i) * x(\lambda) * d\lambda$$

$$\int E^{capteur}(\lambda)_i * y(\lambda) * d\lambda = \int R^{OBJ}(\lambda) * (I^{ext}(\lambda) + S^{SOURCE}(\lambda)_i) * x(\lambda) * d\lambda$$

$$\int E^{capteur}(\lambda)_i * z(\lambda) * d\lambda = \int R^{OBJ}(\lambda) * (I^{ext}(\lambda) + S^{SOURCE}(\lambda)_i) * x(\lambda) * d\lambda$$

by calculating the numerical value corresponding to the left-hand side of the Ei integrated equations with the use of the output parameters of the digital image sensor; and by expressing the two unknown continuous functions $R^{OBJ}(\lambda)$ and $I^{ext}(\lambda)$ with the use of a finite number of interpolation points $(\lambda_j, y_j)$ connected by at least one interpolation function $s(\lambda)$ for maintaining the continuous nature of the said unknown continuous functions $R^{OBJ}(\lambda)$ and $I^{ext}(\lambda)$, the $\lambda_j$ being selected wavelengths in the intersection of the source and sensor spectra and being input parameters of the method, chosen for minimizing the number of interpolation points for a given precision; and by finding the parameters $y_j$ of the curves $R^{OBJ}(\lambda)$ and $I^{ext}(\lambda)$ that minimize the least squares system $\|-A*-X-B\|_2$ resulting from the $E_i$ integrated equations.

15. A method according to claim 2, characterized in that the series of N illuminants is of the same order of magnitude as the number of interpolation points for determining the values of the uniform diffuse reflectance $R^{OBJ}(\lambda)$ at least at one point of the object (30) and of the external illuminant $I^{ext}(\lambda)$.

16. A method according to claim 2, characterized in that it includes a step of determining the values of the uniform diffuse reflectance $R^{OBJ}(\lambda)$ at least at one point of the object (30) and the external illuminant $I^{ext}(\lambda)$ in several spectral bands.

* * * * *